United States Patent
Burger et al.

(10) Patent No.: US 8,580,519 B2
(45) Date of Patent: Nov. 12, 2013

(54) USE OF PLASMA HSP90 RELATED TO MALIGNANCY

(75) Inventors: Angelika M. Burger, Baltimore, MD (US); Edward A. Sausville, Silver Spring, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 230 days.

(21) Appl. No.: 12/515,770

(22) PCT Filed: Nov. 26, 2007

(86) PCT No.: PCT/US2007/085529
§ 371 (c)(1),
(2), (4) Date: Dec. 31, 2009

(87) PCT Pub. No.: WO2008/070472
PCT Pub. Date: Jun. 12, 2008

(65) Prior Publication Data
US 2010/0129829 A1     May 27, 2010

Related U.S. Application Data

(60) Provisional application No. 60/861,166, filed on Nov. 27, 2006.

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS 7,160,885 B2   1/2007   Currie et al.

OTHER PUBLICATIONS

Tockman et al (Cancer Res., 1992, 52:2711s-2718s).*
Ramanathan et al (Cancer Therapy: Clinical, 2005, 11(9): 3385-3391).*
Ripley et al (Journal of Autoimmunity, 2001, 17: 341-346).*
International Preliminary Report on Patentability issued Jun. 3, 2009 (Published Jun. 3, 2009), during the prosecution of International Application No. PCT/US07/85529.
International Search Report issued Jul. 29, 2008 (Published Sep. 25, 2008), during the prosecution of International Application No. PCT/US07/85529.
Nadin et al., "Deoxyribonucleic Acid Damage Induced by Doxorubicin in Peripheral Blood Mononuclear Cells: Possible Roles for the Stress Response and the Deoxyribonucleic Acid Repair Process," Cell Stress Chaperones 2003 Winter; vol. 8(4):361-372.
Ramanathan et al., "Phase I Pharmacokinetic-Pharmacodynamic Study of 17-(Allylamino)-17-Demethoxygeldanamycin (17AAG, NSC 330507), A Novel Inhibitor of Heat Shock Protein 90, In Patients With Refractory Advanced Cancers," Clin Cancer Res. May 1, 2005; vol. 11(9):3385-3391.
Written Opinion issued Jul. 29, 2008 issued during the prosecution of International Application No. PCT/US07/85529.

\* cited by examiner

*Primary Examiner* — Sean Aeder

(57) ABSTRACT

The present invention concerns diagnosing and/or prognosticating cancer in an individual and/or determining response to a Hsp90-interacting therapy in an individual. In particular, the methods and compositions of the therapy relate to levels of Hsp90-α in plasma. Additional methods concern determining levels of Hsp90-associated molecules.

8 Claims, 13 Drawing Sheets

USE OF PLASMA HSP90 RELATED TO MALIGNANCY

This application is a national phase filing under 35 USC §371 of PCT International Application Serial No. PCT/US07/85529, filed Nov. 26, 2007, which claims priority to U.S. Provisional Patent Application Ser. No. 60/861,166, filed on Nov. 27, 2006, both of which applications are incorporated by reference herein in their entirety.

This invention was made with government support under NCA-SAIC subcontract number WSU06043; NCI Grant number CA062487; and NCI Grant No. CA129666. The United States Government has certain rights in the invention.

FIELD OF THE INVENTION

The fields of the present invention include at least molecular biology, cell biology, and medicine, including cancer. In certain fields of the invention, there are methods for diagnosing and/or prognosticating cancer, and/or determining responsiveness of a therapy therefor, based on Heat Shock Protein (Hsp) 90-alpha levels.

BACKGROUND OF THE INVENTION

Biomarkers for cancer diagnosis and treatment prognosis are important in cancer, and biomarkers useful in cancer drug development fall into three distinct categories. Diagnostic biomarkers allow selection of patients that may have an increased potential for clinical response. In many cases, agents aided in use by these markers target some aspect of the biomarker's structure or function. Examples include estrogen receptor (ER) or erbB2 expression in breast cancer in relation to ER antagonists or trastuzumab, respectively, or mutated epidermal growth factor (EGF) receptors in non-small cell lung cancer in relation to gefitinib, an EGF-receptor antagonist (Dalton and Friend, 2006). Other types of biomarkers are proximate indicators of a drug's "landing" on its target. These can be utilized to define dosing interval or avoid toxicity. Relevant markers of this type would include proteosome activity in surrogate tissues such as leukocytes after exposure to bortezomib, the novel proteosome inhibitor. A final category of biomarkers is useful as a measure of disease burden, without specific mechanistic reference to how the drug acts. Examples would include chorionic gonadotropin in germ cell neoplasms or CA125 in ovarian cancers (Dalton and Friend, 2006; Mackay et al., 2005). Novel treatments for cancer frequently advance to the clinic without biological predictors of value owing to the lack of validated markers at the time the drug has been defined to possess satisfactory empirical activity with likely acceptable toxicity. Hsp90-directed drugs represent one such novel class of anti-cancer agents that lacks useful, validated markers of either potential clinical benefit, or of drug action on its target. The development of such a biomarker would be of value to the development of these agents (Zhang et al., 2006; Ciocca and Calderwood, 2006).

Historically, Hsp90 was one of a family of proteins induced by a variety of cell stresses e.g. heat, but also by nutrient depletion or ambient acidity, for example. Hsp90 can constitute up to 1-2% of a cell's soluble protein. An extensive body of data supports the concept that Hsps serve as multicomponent machines, "chaperones", to assist in the proper folding of newly synthesized proteins or refolding of proteins damaged by heat or other stresses, termed "clients" (Ciocca and Calderwood, 2005; Kamal et al., 2004). Hsp90 chaperone function is dependent on its ATP-binding site. When ATP is bound, client protein-Hsp90 complexes in the context of additionally bound "co-chaperone" molecules including Hop40, Hsp70, p50 and p23, can form (Ciocca and Calderwood, 2005; Burger, 2006). Following ATP hydrolysis, a properly folded molecule is released from the Hsp90 complex. If the client protein is improperly or incompletely folded, it is subject to ubiquitination, followed by proteosome-mediated degradation (Kamal et al., 2004; Burger, 2006). Over 500 Hsp90 client proteins have been identified including hormone receptors such as estrogen receptor (ER), progesterone receptor (PR), glucocorticoide receptor (GR) (Pratt and Toft, 2003). Of great interest to cancer treatment is that many of the "clients" of Hsp90 that are processed through its folding function include oncogene products (e.g. c-erbB2, bcr-abl, npm-alk, c-raf, v-src), important regulators of cancer cell growth and cell cycle progression (e.g. cdk4, EGF-R, IGF1-R, telomerase), or apoptosis-related signaling (e.g., akt, mutant p53). This biology has increased enthusiasm for defining modulators of Hsp90 function as a strategy to attack multiple Hsp90 clients (Kamal et al., 2004; Burger, 2006; Pratt and Toft, 2003).

Hsp90 itself exists in two major isoforms, Hsp90α (stress-induced, affording cytoprotection) and Hsp90β (constitutively expressed form, accompanying cellular transformation). Biochemical and functional differences as well as differences in the expression mechanisms and induction of the two isoforms are known (FIG. 2) (Daniel et al., 2005; Sreedhar et al., 2004; Picard, 2004). Hsp90α is encoded by 10 exons in a 5.33 kb genomic DNA and Hsp90β by 11 exons in a 6.88 kb DNA stretch. The human isoforms are about 85% homologous and share a common N-terminal ATP- and geldanamycin binding site (Sreedhar et al., 2004). Their middle domain is the site of client protein binding, and the C-terminal domain is responsible for binding co-chaperone molecules. The main functional difference appears to be that Hsp90α dimerizes more readily than Hsp90β (Sreedhar et al., 2004). Additional Hsp90 analogues are Grp94 (induced, antigen presentation) in the endoplasmic reticulum and TRAP1 (=Hsp75, constitutive active, cell cycle regulation) in the mitochondrial matrix (FIG. 2) (Sreedhar et al., 2004; Picard, 2004). Evidence has emerged that Hsp90α and β are differently expressed in tumors. Hsp90α expression is associated with poor prognosis in breast and pancreas carcinoma, whereas Hsp90β expression has been implicated in tumor drug resistance (Ciocca and Calderwood, 2005; Sreedhar et al., 2004). A very recent study showed that Hsp90α but not Hsp90β is found on the cell surface of invasive fibrosarcoma cells and binds to matrix metalloproteinase 2 in a way that is disrupted by geldanamycins (FIG. 2) (Picard, 2004; Eustace et al., 2004). This "translocalization of Hsp90" to the outside of the cell and its resulting potential impact on conformational folding and interaction with proteins of the extracellular micro-environment, open the possibility that Hsp90α and extracellular clients could be used as circulating response markers of geldanamycin treatment.

Hsp90 antagonists and cancer therapy are further related in the invention. The benzoquinoid ansamycins (BA) were originally defined as anti-tumor antibiotics produced by *Streptomyces* species, which had the unique property of causing reversion of the transformed phenotype of v-src expressing cells. Index members of the class include herbimycin and geldanamycin (DeBoer et al., 1970; Whitesell et al., 1994). Because BAs decreased phosphotyrosine levels in treated cells, they were originally considered "tyrosine kinase antagonists" (Sakagami et al., 1999). However, mechanistic studies revealed that there was little, if any significant activity in causing tyrosine kinase inhibition in purified kinase assays.

Moreover, the physical mass of tyrosine kinases decreased in BA-treated cells, leading to the proposal that BAs somehow affected the "intracellular environment" of the tyrosine kinases (Sakagami et al., 1999). To address the basis for these phenomena, Neckers and colleagues at the National Cancer Institute created a solid-phased geldanamycin derivative, and demonstrated selective adsorption of a 90 kd protein that was identified as Hsp90 (Whitesell et al., 1994). Crystallographic studies by Pavletich et al. later confirmed that BAs can bind with high affinity to a pocket on the surface of Hsp90 (Stebbins et al., 1997). Moreover, a basis for tumor cell selectivity of BAs was established with studies performed by Kamal et al. who showed that affinities of BAs to Hsp90 purified from tumors, as opposed to Hsp90 from normal cells, differ (Kamal et al., 2003). The Kd of Hsp90 for geldanamycins was noteworthily lower in tumor cells, and this correlated with an increased BA-sensitive Hsp90 associated ATPase activity in the latter cell types (Kamal et al., 2003). Thus, BAs have emerged as lead structures to perturb the interaction of Hsp90 with client proteins in a way that is correlated with their capacity to inhibit tumor cell growth.

Geldanamycin itself was unsuitable for formulation, and had severe hepatotoxicity in preclinical toxicology studies. Subsequently, 17-allylamino, 17-demethoxygeldanamycin (17AAG), and 17-dimethylaminoethylamino, 17-demethoxygeldanamycin (17 DMAG) were identified by the inventors and others as analogs suitable for formulation and clinical testing (Burger et al., 2004; Smith et al., 2005; Hollingshead et al., 2005). In addition, mechanistic studies showed that 17AAG and 17DMAG functioned as prototypical Hsp90 antagonists in a way exactly analogous to geldanamycin, with activity in preclinical animal models and evidence of anti-angiogenic activity (Burger et al., 2005; Smith et al., 2005; Hollingshead et al., 2005; Kaur et al., 2004; Nimmanapalli et al., 2001; Munster et al., 2001; Solit et al., 2002; Eiseman et al., 2005).

Other classes of Hsp90 antagonists have been discovered in nature (e.g., radicicol) or designed from structural considerations (e.g., EC69, EC97) (Zhang et al., 2006). While a non-geldanamycin chemotype of Hsp90 antagonist would be greatly interesting, none of these other structural classes has yet to reach the clinic, and therefore strategies to define potential markers for Hsp90 modulator effect must at the present time be focused on BAs. However, these strategies will be very useful as clinical trial opportunities are evolved using other chemotypes.

There are currently employed response markers in clinical trials of BAs. While 17DMAG has just entered phase I clinical trials, 17AAG has advanced to phase II clinical trials and has been tested for efficacy in several hundred cancer patients to date. Phase I clinical trial results that include pharmacokinetic and pharmcodynamic endpoint evaluation have been published (Grem et al., 2005; Banerji et al., 2005; Matthew et al., 2005). The pharmacokinetic data showed that drug levels were achieved well in excess of where modulation of Hsp90 associated client proteins is observed in vitro and in in vivo animal model experiments. In the latter studies, the pharmacodynamic activity of the drug was evaluated by measuring Hsp70 activation and/or degradation of cyclin-dependent kinase 4 or Raf-1.

Encouragingly, pharmacodynamic marker studies in a few but statistically insignificant number of cases did reveal that in the tumor cell compartment, 17AAG has been accompanied by changes in Hsp90 client proteins, particularly Raf-1 and CDK4 (Grem et al., 2005; Banerji et al., 2005; Ramanathan et al., 2005; Matthew et al., 2005). Of interest clinically, although no formal responses have been observed, in the solid tumor patients several patients with renal carcinoma and melanoma have had very protracted periods of disease stability, in one noteworthy case of melanoma out to years of treatment (Banerji et al., 2005).

Biomarker studies accomplished by Western blot of samples from either tumor biopsies or peripheral blood mononuclear cells (PBMC) are both laborious and time consuming. In addition, tumor biopsies are only available from a minority of patients, whereas PBMCs represent at best a surrogate for the tumor, and their use for longitudinal studies may be somewhat limited due to the relatively large amount of blood required (Ciocca and Calderwood, 2005).

This led to the recent exploitation of two new biomarkers by Burrows and co-workers, namely insulin-like growth factor binding protein-2 (IGFBP2) and HER-2 extracellular domain that can be readily detected in patient sera by ELISA (Ciocca and Calderwood, 2005). Burrows et al. argue that both proteins are secreted and might be suitable to predict BA response because they are regulated by Hsp90 client proteins and they demonstrate by using a breast cancer xenograft model (BT474) and 5 normal and 20 cancer patient (not treated) sera that IGFBP2 and HER-2 extracellular domain might be valuable pharmacodynamic tools in clinical trials of Hsp90 inhibitors (Ciocca and Calderwood, 2005).

Taking all pharmacodynamic endpoint studies together, neither in animal tumor models nor in patients is there a clear, validated indicator that has sufficient statistical power to predict for sensitivity to BAs. Therefore it would be highly desirable to develop a biomarker of potential responsiveness to BA action, ideally the direct drug target Hsp90, that can be used to predict clinical benefit, or in a functional sense that the drug having had an effect on the tumor's biology at the dose and schedule studied. As recent evidence described that Hsp90α is secreted into the extracellular milieu, an examination of the detectable Hsp90 isoform in patient plasma is informative as to dynamics of Hsp90 modulator action.

SUMMARY OF THE INVENTION

The present invention generally concerns diagnosing, prognosticating, and/or monitoring cancer therapy in an individual. In particular aspects of the invention, the invention generally concerns the level of Hsp90α in a biological fluid sample of an individual that has cancer or that is suspected of having cancer or is at risk for having cancer, including individuals that have never been diagnosed with cancer and individuals that have been diagnosed with cancer before. The individual may be of any kind, but in particular aspects the individual is a mammal, such as a human, dog, cat, horse, cow, goat, sheep, and so forth.

In a particular embodiment of the invention, the method comprises steps of isolating a predominantly non-cellular fraction of a body fluid obtained from an individual wherein the non-cellular fraction may be plasma, serum, or other non-cellular body fluid. In specific embodiments of the invention, the method comprises steps of obtaining plasma or serum as at least part of the determination of the level of Hsp90α. In a specific embodiment, the body fluid from which the sample is obtained from an individual comprises blood, which may be further processed to obtain plasma or serum.

In certain aspects, methods of the invention concern determining quantitatively the amount or concentration of Hsp90α from a sample of plasma, serum, pleural effusions, ascites or other non-cellular body fluid wherein the amount or concentration of Hsp90α thereby diagnoses, evaluates, infers, or monitors cancer or a susceptibility thereto, and/or monitors response to cancer therapy in an individual. In alternative embodiments, the sample is assayed for qualitative or both quantitative and qualitative determination of Hsp90α. In particular aspects, methods of the invention relate to determining quantitatively the amount or concentration of Hsp90α from plasma or serum of an individual, wherein the plasma or serum is obtained from the blood of the individual, for example.

In particular cases, Hsp90 levels that are measured are those that are extracellular, and in specific cases the Hsp90 that is measured relates to Hsp90 that folds extracellular proteins, such as extracellular matrix proteins, for example. In particular cases, the level of extracellular Hsp90 in an individual is modulated, such as increases or decreases, upon exposure of the individual to Hsp90-interacting therapies, and in specific embodiments the modulation in extracellular Hsp90 is not related to cell death, although in alternative embodiments the modulation in extracellular Hsp90 is related to cell death.

In other embodiments of the invention, an individual that has cancer or that is suspected of having cancer or is at risk for developing cancer is administered an Hsp90-interacting drug. The drug may be administered to the individual in any suitable manner, but in specific embodiments the drug is administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular embodiments, a sample is taken from the individual prior to administration of the drug. Although the sample may be of any suitable kind, in specific aspects of the invention the sample comprises blood, plasma, or serum. In further aspects, a sample is obtained prior to administration of the drug to provide a baseline level of Hsp90α. In certain aspects, such a baseline level is then utilized in comparison of Hsp90α levels from a corresponding sample from the individual subsequent to administration of the Hsp90-interacting drug.

In an additional embodiment the Hsp90-interacting drug is an inhibitor of Hsp90. In a specific embodiment the inhibitor of Hsp90 binds to Hsp90 and decreases its chaperone function. The inhibitor of Hsp90 may bind the ATP-binding site, a C-terminal section, such as the region where Hsp90 interacts with an associated molecule, or the BA-binding pocket on the surface, for example.

In particular aspects of the invention, the level of Hsp90 is measured in an individual before and after an Hsp90-interacting therapy. The amount of time between measuring the level from an individual before the therapy and the time of the therapy itself may vary, but in particular aspects it is no less than between about 30 minutes and about 1 day and no greater than between about 72 hours and about 14 days, for example. The amount of time between administration of the therapy and measurement of the Hsp90 level thereafter may vary, but in particular aspects it is no less than between about 30 minutes and 3 days and no greater than between about 72 hours and about 18 days, for example.

Thus, in particular embodiments of the invention, the relative and/or absolute concentration of Hsp90α from the plasma, serum, pleural effusion, ascites, or other non-cellular body fluid obtained from an individual after administration of an Hsp90-interacting drug is determined when compared to plasma, serum or other non-cellular body-fluid type obtained from the same individual prior to administration of an Hsp90-interacting drug. The relative and/or absolute concentration of Hsp90α from the plasma, serum, or other non-cellular body fluid prior to and subsequent to administration of the drug is detectably changed by standard methods in the art or is not detectably changed by standard methods in the art. In specific embodiments, the change is an increase in the level of Hsp90α and in alternative embodiments the change is a decrease in the level of Hsp90α. In further specific embodiments, an increase in Hsp90α level indicates that the individual is responsive to the Hsp90-interacting drug therapy. An increase in Hsp90α level over a known reference amount for an individual that is not administered an Hsp90α-interacting drug provides information concerning the presence of cancer, the type of cancer, the stage of cancer, tumor burden, and/or prognosis for the individual, in specific embodiments of the invention. For example, an increase in plasma Hsp90α in an individual suspected of having cancer when compared to a reference amount indicates that the individual has cancer and, in specific embodiments, that the individual has a certain type of cancer, certain stage of cancer, certain tumor burden, and so forth. In other exemplary embodiments, an increase in plasma Hsp90α in an individual known to have cancer indicates that the individual has a certain type of cancer, certain stage of cancer, certain tumor burden, and so forth.

A particular embodiment of the invention is determining the type of cancer by determining quantitatively the amount or concentration of Hsp90α from a body fluid, such as plasma or serum, of an individual that has cancer or that is suspected of having cancer that has been administered an Hsp90-interacting drug. In specific embodiments, a change in Hsp90α levels is an increase of Hsp90α in plasma or serum of an individual, and in alternative embodiments there is no change or a decrease in the level of Hsp90α in the plasma or serum of an individual. For example, different forms of cancer may be more or less responsive to Hsp90-interacting drug therapies than other forms of cancer. The change in Hsp90α levels in the plasma or serum of an individual that has cancer or that is suspected of having cancer after administration of the Hsp90-interacting drug therapy may identify the type of cancer.

A particular embodiment of the invention is determining cancer progression by determining quantitatively the amount or concentration of Hsp90α from plasma or serum of an individual that has cancer or that is suspected of having cancer that has been administered an Hsp90-interacting drug. In specific embodiments, a change in Hsp90α levels is an increase of Hsp90α in plasma or serum of an individual, and in alternative embodiments there is no change or a decrease in the level of Hsp90α in the plasma or serum of an individual. For example, different stages of cancers may be more or less responsive to Hsp90-interacting drug therapies than other stages of cancers. The change in Hsp90α levels in the plasma or serum of an individual that has cancer or that is suspected of having cancer after administration of the Hsp90-interacting drug therapy may identify the progression of cancer.

In particular embodiments, the Hsp90α polypeptide is detected using an agent that interacts with Hsp90α polypeptide. In specific embodiments, the agent is an antibody that binds Hsp90α or Hsp90α fragments. The agent may comprise a label used for detection, such as a chemiluminescent tag, colorimetric tag, fluorescent tag, or radioactive label, for example.

Another embodiment of this invention is a method of diagnosing cancer progression by determining quantitatively the amount or concentration of Hsp90α from the plasma or serum of an individual after administering a composition comprising an Hsp90-interacting drug with a known anti-cancer or anti-proliferative compound such as a tyrosine kinase inhibitor, paclitaxel, or doxorubicin.

Another embodiment of this invention is a method of diagnosing cancer progression by determining quantitatively the amount or concentration of Hsp90α from the plasma or serum of an individual after administering a combination of an Hsp90-interacting drug in combination with radiation therapy, for example conventional radiation therapy.

In particular embodiments, methods of the invention concern diagnosing the presence or progression of cancer by determining quantitatively the amount or concentration of Hsp90α-interacting proteins from the plasma or serum of an individual that has cancer or is suspected of having cancer. In specific embodiments, the Hsp90α-interacting proteins are extracellular proteins such as MMP2, VEGF, TGF-beta, IGFI/II, EGF, or uPA, or other steroid hormone receptors or oncogene products (see, for example, Zhao et al., Cell, 120, 715, 2005, which is incorporated herein by reference in its entirety), for example. In alternate embodiments, the Hsp90α-interacting proteins are Hsp90 co-chaperone proteins, such as Hsp Organizing Protein (HOP), Hsp70, CHIP, or p23, for example. Alternatively, the Hsp90α-interacting protein is vis a vis a protein-protein assembly, such as with cyclin D, or, alternatively, a protein-cofactor assembly, such as, for example, with EIF2alpha or heme, or further a protein assembly such as with ras or raf.

Thus, in specific embodiments the invention concerns biomarkers that classify cancers, guide treatment decisions, and/or predict response, and such biomarkers are useful for development of novel therapeutic agents. Benzoquinone ansamycin (BA) drugs such as 17-allylamino, 17-demethoxygeldanamycin (17AAG), and its orally bioavailable congener 17-dimethylaminoethylamino, 17-demethoxygeldanamycin (17DMAG), have recently entered clinical trials. The target of BAs is Hsp90 stress response protein. The inventors and others have found that the α isoform of Hsp90 is secreted into the extracellular milieu by tumor cells, in specific aspects. The inventors have demonstrated that the secretion of the α but not β isoform is induced in response to 17AAG. This raises the possibility that secreted Hsp90α could be a plasma marker of tumor response to BAs in patients. Hsp90 has chaperone function and forms complexes with growth factor receptors and oncogene products expressed in tumor cells. Thus, in specific embodiments, the spectrum of Hsp90α-associated molecules detectable in complexes isolated from plasma of tumor-bearing patients before and after treatment is qualitatively different and is distinct from Hsp90α-related complexes obtained from normal and tumor cell lysates. In particular aspects of the invention, the circulating plasma Hsp90α isoform is an important and hitherto unexploited marker that informs at least as to the presence of a cancer in a human subject, and that in certain patients modulation of Hsp90α plasma levels serves as a pharmacodynamic marker of Hsp90 antagonist effect on the tumor cell.

In additional embodiments of the invention, circulating Hsp90α and Hsp90α isoform-associated molecules provide information about the presence of tumors in mice bearing human tumor xenografts. In certain embodiments of the invention, there is assessment of the presence of extracellular Hsp90α in cell line and mouse models in response to the exemplary BA drugs. This information provides additional evidence that Hsp90α serves at least as a diagnostic marker for malignancy and a prognostic marker for responsiveness to Hsp90-directed agents. The animal model studies further characterize whether the levels of Hsp90α determined in plasma from cancer patients that are responsive to BA drugs are a BA-specific or more general biomarker of cancer treatment effects in humans.

In additional embodiments of the invention, it is determined how Hsp90α-associated molecules in the extracellular milieu differ qualitatively from Hsp90α-associated molecules detected in cell lysates and it is confirmed in plasma samples from cancer patients. Specific embodiments of the invention include at least establishment of circulating Hsp90α as a biomarker for detection, prediction and measurement of response to BAs in exemplary preclinical model systems. Other embodiments concern the specific effect of Hsp90 antagonists on Hsp90α isoform secretion into the extracellular compartment of tumor cells in vitro (medium) and in nude mice (plasma) bearing human tumor xenografts in vivo. In other embodiments, there is identification of Hsp90α-associated molecules in the extracellular compartment of tumor cells in vitro (serum-free medium) and in animals (plasma) bearing human tumor xenografts in vivo by utilizing proteomic techniques, for example.

In another embodiment of the invention, secreted Hsp90α-associated molecules are compared before and after treatment with a BA to Hsp90α and Hsp90 "bulk" associated molecules in whole cell lysates of human tumors propagated in cell culture or as xenografts. In an additional embodiment of the invention, there is assessment of Hsp90α as a biomarker for detection, prediction and measurement of response to BAs in patients.

In a further embodiment of the invention, Hsp90α plasma levels are compared in cancer patients with Hsp90α levels from banked plasma from non-tumor bearing hosts, for example. Other embodiments include the measurement of Hsp90α levels in plasma of tumor bearing hosts before and after treatment with BAs.

In particular embodiments of the invention, any chemotherapeutic increases Hsp90alpha levels and the effect of the administration of that chemotherapeutic is prognostic for the therapy provided by same.

In one embodiment of the invention, there is a method of monitoring a cancer therapy in an individual, comprising the step of determining the level of Hsp90 in the plasma or serum of the individual, wherein the therapy is a Hsp90-interacting therapy. In a specific embodiment, the method is further defined as obtaining a sample comprising blood from the individual and processing the sample to obtain plasma or serum. The Hsp90 may be further defined as Hsp90α, in specific embodiments. The Hsp90 may be extracellular, in other specific embodiments. In another specific embodiment of the invention, the Hsp90-interacting therapy comprises an inhibitor of Hsp90. The Hsp90-interacting therapy comprises one or more benzoquinoid ansamycins, in particular aspects of the invention, and the Hsp90-interacting therapy may comprise 17-allylamino, 17 demethoxy geldanamycin, CF237, EC69, EC97, or PU3, in particular aspects. Synthetic drugs may be employed. Exemplary drugs may be obtained commercially, such as from Vernalis®, for example.

In certain aspects of the invention, the determining step is further defined as comparing the Hsp90 level in the sample to a control, for example a sample from the individual, wherein the sample is obtained from the individual prior to administration the Hsp90-interacting therapy. The control may be from one or more individuals without cancer, in specific embodiments. In certain aspects of the invention, when the level of Hsp90 is increased at least two-fold over a control, the cancer is responsive to the therapy. In alternative aspects, the sample is compared to a sample obtained from the individual receiving a cancer therapy prior to receiving the therapy.

The level of Hsp90 in the plasma or serum may be determined by measuring Hsp90 protein levels, in particular embodiments. The Hsp90 protein levels may be measured by one or more immunoassays, such as, for example, ELISA, western blot, immunohistochemistry, immunofluorescence, affinity purification (for example, solid phase derivative of geldanamycin for enrichment strategy (see Whitesell et al., PNAS, 91, 8324, 1994)), or fluorescence resonance energy transfer (FRET) imaging.

The cancer may be breast cancer, lung cancer, brain cancer, skin cancer, prostate cancer, pancreatic cancer, colon cancer, bone cancer, kidney cancer, bladder cancer, spleen cancer, leukemia, lymphoma, ovarian cancer, testicular cancer, cervical cancer, gall bladder cancer, head and neck cancer, stomach cancer, thyroid cancer, pituitary gland cancer, eye cancer, melanoma, sarcoma (Kaposi's sarcoma, soft tissue sarcoma, for example), or esophageal cancer.

Methods of the invention may further comprise the step of determining the level of a Hsp90-associated molecule. The Hsp90-interacting molecule may be Mmp2, VEGF, uPA, IGFI/II, IGFBP1-6, IGFBP-rP1-5, TGF-beta, TNF-alpha, or EGF, for example.

In an additional embodiment of the invention, there is a method of diagnosing cancer in an individual, comprising the step of determining the level of Hsp90 in the plasma or serum of the individual. The method may be further defined as obtaining a sample comprising blood from the individual and processing the sample to obtain plasma or serum, in certain aspects.

In another embodiment, there is a method of prognosticating cancer in an individual, comprising the step of determining the level of Hsp90 in the plasma or serum of the individual. The method may be further defined as obtaining a sample comprising blood from the individual and processing the sample to obtain plasma or serum.

In a further embodiment, there is a method of monitoring a cancer therapy in an individual, comprising the step of determining the level of one or more Hsp90-associated molecules in the plasma or serum of the individual, wherein the therapy is a Hsp90-interacting therapy, for example.

In a further embodiment of the invention, there is a method of diagnosing cancer in an individual, comprising the step of determining the level of one or more Hsp90-associated molecules in the plasma or serum of the individual.

In an additional embodiment of the invention, there is a method of prognosticating cancer in an individual, comprising the step of determining the level of one or more Hsp90-associated molecules in the plasma or serum of the individual.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 3A shows baseline expression of Hsp90 and the α, β isoforms in whole cell lysates (WCL) where actin was used as loading control. FIG. 3B shows baseline expression of Hsp90 and the α, β isoforms as well as MMP2 in serum-free, conditioned medium (SFM) (Veerasamy et al., 2006). Red box highlights the lack of Hsp90β expression SFM.3 FIG. 3C provides the effects of 17-AAG (at TGI=concentration causing total growth inhibition) on total Hsp90, Hsp90α and β, as well as on latent (72 kD) and active MMP2 (66 kD) in serum-free, conditioned medium (SFM) of MEXF276L cells (Veerasamy et al., 2006). FIG. 3D provides the effects of 17AAG (TGI) on the cell cycle distribution of MEXF276L cells. A significant percentage of apoptotic cell debris (sub G1 fraction, grey arrow) compared to control cells is only seen at 48 hrs after treatment with 17AAG.

DETAILED DESCRIPTION OF THE INVENTION

I. Definitions

Figure 1:
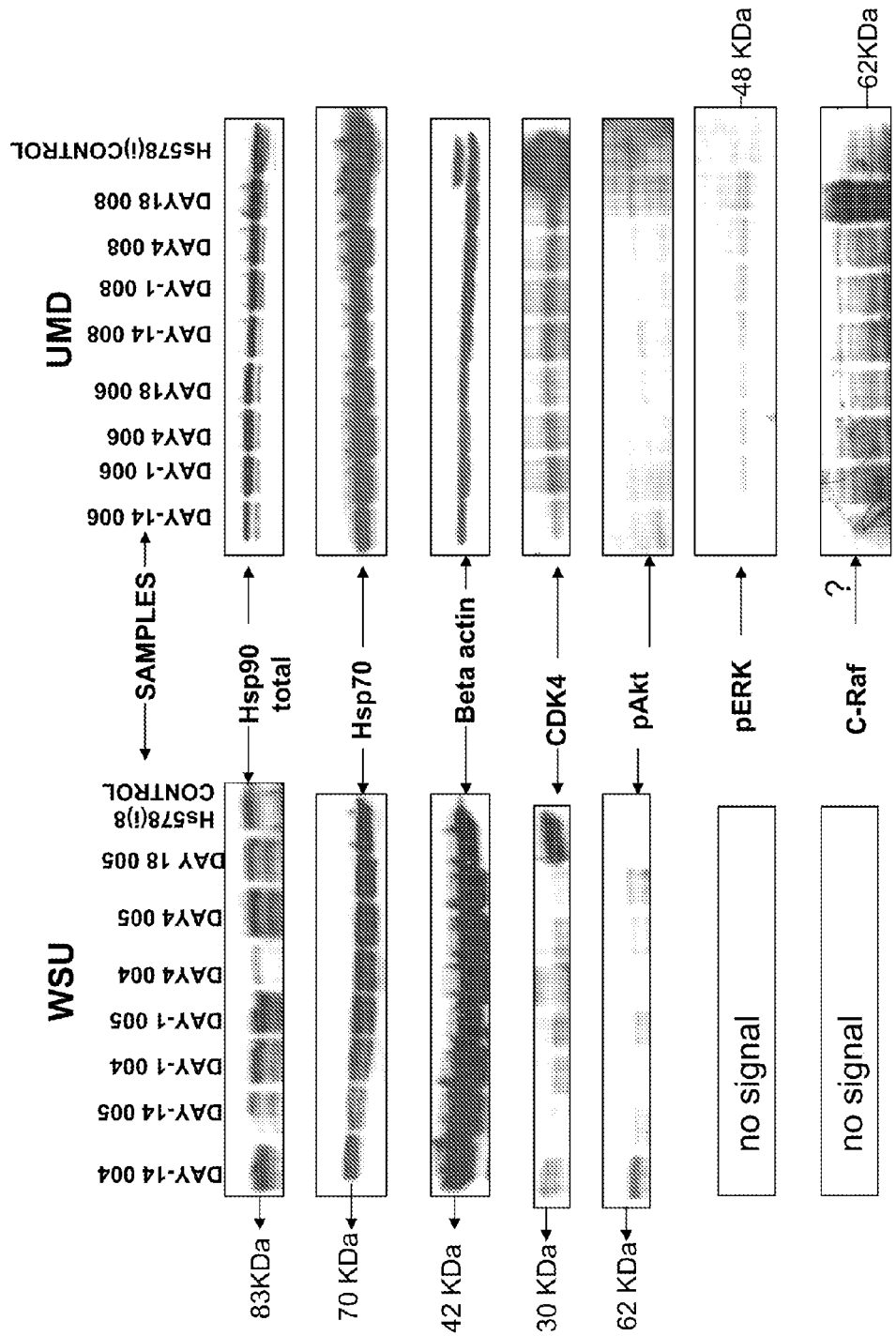
FIG. 1 shows an exemplary method for determining response to 17AAG in western blots of PBL lysates.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "extracellular" is defined as being located outside of a cell or cells. In a specific embodiment, Hsp90α may be located extracellularly or intracellularly in relation to a cancer presence, prognosis, or therapy. In the present invention, the extracellular Hsp90α upon processing of a blood sample is the plasma level Hsp90α. In specific cases, addition of an Hsp90-interacting therapy results in an increase in Hsp90 levels in the plasma, and in further cases the therapy directly or indirectly results in intracellular Hsp90 translocation extracellularly.

The term "Hsp90-interacting therapy" is defined as any agent that directly binds to Hsp90 polypeptide. Such an agent can be an organic or non-organic small molecule, ionic or non-ionic small molecule, a naturally or non-naturally occurring macromolecule, or a polypeptide that can be naturally or non-naturally modified, for example. In certain embodiments, the agent inhibits the function of Hsp90 (including HSP90α) at least partially. In other embodiments, Hsp90 function is not inhibited by the agent. In a particular embodiment, the therapy comprises one or more benzoquinoid ansamycins.

The term "Hsp90 inhibitor" is any agent that binds Hsp90 polypeptide and reduces at least in part its activity. Such an agent can be an organic or non-organic small molecules, ionic or non-ionic small molecule, a naturally or non-naturally occurring macromolecule, or a polypeptide that can be naturally or non-naturally modified, for example.

The term "isoform" refers to a different version of a protein that may be produced by different genes or from the same gene by alternative splicing as defined by the Unified Medical Language System at the National Library of Medicine. In certain embodiments isoforms may have the same function, and in alternate embodiments protein isoforms may have different functions.

The term "plasma" as used herein refers to straw-colored liquid in which blood cells are suspended. In specific embodiments, plasma that was obtained from an individual such as a patient or mouse blood for assays was processed by adding sodium citrate or sodium heparin to prevent clotting, for example.

The term "serum" as used herein refers to blood plasma in which clotting factors, including the exemplary fibrin, have been removed.

II. Embodiments of the Invention

In particular embodiments of the invention, Hsp90α isoform is detectable in body fluid, such as human plasma, for example, and changes in its level can predict the presence or course of cancer and its treatment response. Hsp90 is a chaperone molecule whose proper function is necessary for the folding of "client" proteins. Hsp90 is an abundant cellular protein that exists mainly as a dimer between an alpha and beta isoforms, although in alternative embodiments it exists in homodimers of alpha and beta. The alpha isoform is known to be located in the extracellular environment of tumor cells, although Hsp90β is not. 17-allylamino, 17demethoxy geldanamycin (17AAG) is an exemplary drug known to bind to the N-terminus of Hsp90 that harbors an ATPase activity that is identical in both Hsp90 isoforms. 17AAG is known to cause inhibition of tumor cell growth by affecting the ability of Hsp90 to fold associated molecules important in cancer growth and progression. It was observed that 17-allylamino, 17demethoxy geldanamycin (17AAG) causes an increase in extracellular Hsp90α isoform in cultured cells. The inventors therefore applied this observation to specimens collected from patients who received 17AAG after a period of baseline observations. Administration of 17AAG was followed by an increase in plasma Hsp90α isoform in patients who in 3/3 exemplary cases had some evidence of clinical response (for example, shrinkage in 2/3; attenuation of CT scan image consistent with tumor necrosis in 1 of 3). Therefore, in particular aspects of the invention, individuals with cancer express plasma Hsp90α isoform, and modulation of plasma Hsp90α isoform levels in response to administration of Hsp90-interacting therapy is one exemplary way of predicting clinical responsiveness of tumors to Hsp90-interacting drugs, for example. The inventors therefore defined in athymic nude mice bearing human tumor xenografts that human Hsp90α can be detected in the plasma of mice. Thus, in additional embodiments plasma Hsp90α and its associated binding molecules can serve as exemplary markers of the presence of cancer and/or of the overall burden of tumor in an organism, for example.

In particular embodiments, the method comprises isolating a predominantly non-cellular fraction of a body fluid obtained from an individual, wherein the non-cellular body fluid may comprise plasma, serum or another body fluid. In particular embodiments, the non-cellular fraction is isolated by centrifugation of a cell-comprising body fluid such as blood, or by other means known to the art such as, but not limited to, by passing the body fluid through a filter or otherwise size fractionating or density fractionation to separate the body fluid, whereby the cellular and non-cellular components of the body fluid are separated and the non-cellular fraction is isolated. In preferred embodiments, plasma is isolated from whole blood through centrifugation. Serum can be further obtained by removing clotting factors such as fibrin thereby allowing blood to clot. In particular embodiments, either fresh (i.e., not frozen at any time) plasma or serum samples, or frozen and subsequently thawed plasma or serum samples may be used.

III. Hsp90

In specific embodiments, the present invention determines the levels of an isoform of Hsp90 in the plasma or serum of an individual to diagnose, prognosticate, and/or monitor the presence of cancer and/or the overall tumor burden of an individual. In certain embodiments, the isoform of Hsp90 is Hsp90α. In alternate embodiments, the isoform is Hsp90β and/or another Hsp90 isoform.

In specific embodiments, the term Hsp90 polypeptide refers to a protein chaperone that assists in the folding of polypeptides into their mature, properly folded form. In a particular embodiment, an isoform of Hsp90, Hsp90α, as represented in exemplary National Center for Biotechnology Information's GenBank® database Accession No. NM_001017963 (nucleotide sequence is SEQ ID NO:1, and amino acid sequence is SEQ ID NO:2); NM_005348 (nucleotide sequence is SEQ ID NO:3, and amino acid sequence is SEQ ID NO:4); and/or BC121062 (nucleotide sequence is SEQ ID NO:5, and amino acid sequence is SEQ ID NO:6) are utilized. In an alternate embodiment, an isoform of Hsp90, Hsp90β, of GenBank® Accession No. AF275719 (nucleotide sequence is SEQ ID NO:7, and amino acid sequence is SEQ ID NO:8) or of GenBank® Accession No. S70561 (nucleotide sequence is SEQ ID NO:9, and amino acid sequence is SEQ ID NO:10) is utilized. Furthermore, those skilled in the art will appreciate that other isoforms of Hsp90 that are as yet undisclosed or undiscovered, may be used in the methods and compositions disclosed herein.

In other specific embodiments, the term Hsp90 polynucleotide or Hsp90 nucleic acid refers to any DNA sequence that is substantially similar to a DNA sequence encoding an Hsp90 gene product. The term also refers to RNA sequences compatible with such DNA sequences. In a specific embodiment, a polynucleotide of Hsp90α is utilized. In an alternate embodiment, a polynucleotide of Hsp90β is utilized. Examples of other nucleotide and amino acid sequences include Mmp2 (NM_004530; nucleotide sequence is SEQ ID NO:11, and amino acid sequence is SEQ ID NO:12) for exemplary nucleotide and amino acid sequences and for another exemplary amino acid sequence, AAH02576 (SEQ ID NO:13).

IV. Hsp90-Interacting Therapies

Levels of Hsp90 in the invention may be monitored in relation to any Hsp90-interacting therapy, and in specific embodiments the Hsp90-interacting therapy is an Hsp90 inhibitor that inhibits at least partially the activity, stability, dimer formation and/or expression of Hsp90. In certain aspects, the Hsp90-interacting therapy binds directly to Hsp90, although in alternative embodiments it binds to Hsp90 indirectly and/or affects Hsp90 by acting upstream of Hsp90. In particular cases, however, the Hsp90-interacting therapy blocks the ATP site, such as by occupying the ATP site. Alternatively, Hsp90-interacting therapy interferes with the complexation of Hsp90 with co-chaperone molecule, such as but not limited to HOP, P23, HSP70, and CHIP, for example. Further, Hsp90-interacting therapy inhibits the complexation of a client protein with Hsp90 and its associated co-chaperone molecule.

In another embodiment, the tetratricopeptide repeat (TPR) motif is a site of Hsp90 inhibition. Hsp90 is a large protein with three structural domains: the N-terminal ATP- and geldanamycin-binding site; the middle domain, which is the major site of client protein binding; and the C-terminal domain, which is responsible for binding TPR-containing co-chaperones. The tetratrico peptide repeat (TPR) motif is a sequence of ~34 amino acids containing the consensus residue -W-LG-Y-A-F-A-P-, which occurs in tandem arrays and is present in over 800 different proteins. TPR motif-containing proteins act as scaffolds for the assembly of different multiprotein complexes and are involved in a variety of biological processes, such as cell cycle regulation, transcriptional control, protein transport and folding. Known Hsp90 binding partners with a TPR are the co-chaperone HOP and the ubiquitin E3 ligase CHIP. The latter has been demonstrated to enforce the degradation of c-erbB2 if Hsp90 is inhibited by geldanamycin. It is therefore apparent that Hsp90 is potentially key to the function of a huge number of both "housekeeping" and "regulatable" proteins of which many are yet to be characterized (Kamal et al., 2004; Sreedhar et al., 2004; Picard, 2004; Jackson et al., 2004).

Although in particular aspects the Hsp90-interacting therapy can penetrate into a cell to affect intracellular Hsp90, in other aspects the Hsp90-interacting therapy generally or specifically affects extracellular Hsp90. In particular cases, the Hsp90-interacting therapy that generally or specifically affects extracellular Hsp90 does not enter the cell, and in further specific aspects the Hsp90-interacting therapy that generally or specifically affects extracellular Hsp90 is insoluble.

In particular embodiments, the Hsp90-interacting therapy comprises one or more benzoquinoid ansamycins. In specific embodiments of the invention, the Hsp90 inhibitor is an ansamycin antibiotic such as geldanamycin or herbimycin A, for example. In further embodiments, the Hsp90 inhibitor is a derivative of geldanamycin such as 17-(allylamino)-17-desmethoxygeldanamycin (17-AAG), CF237, or DMAG or other benzoquinioid ansamycins, for example. In another embodiment, the Hsp90 inhibitor is radicicol a macrocyclic antibiotic produced by fungi, or an oxime derivative of radicicol, for example. In yet another embodiment, the Hsp90 inhibitor is a chimera of geldanamycin and radicicol such as raderster, radamine, or radanamycin or a derivative of such, for example. Agents such as geldanamycin and radicicol inhibit Hsp90 function by binding the ATP site located at the N-terminal, disrupting ATPase activity that is essential for its chaperone activity.

In another embodiment of the invention, the Hsp90 inhibitor is a coumarin antibiotic such as novobiocin, coumermycin A1, or chlorobiocin, for example. In another embodiment of the invention, the Hsp90 inhibitor is cisplatin. Agents such as novobiocin and cisplatin bind to the C-terminus of Hsp90 and inhibit its function.

In an additional embodiment of the invention, the Hsp90 inhibitor is a purine-based synthetic small molecule, such as PU3 or PU24FC1, for example. In another embodiment of the invention, the Hsp90 inhibitor is a synthetic small molecule such as SNX-5422. SNX-5422, SNX-5542, EC69, and EC97 are potent, novel, highly specific, water soluble and orally active small molecule inhibitors of Hsp90. In alternate embodiments, the Hsp90 inhibitor is a peptide that binds the N-terminal ATP binding pocket or co-chaperone binding site in a manner that preferably results in an inhibition of Hsp90 to regulate one or more client proteins (e.g., the amount of and/or the activity of a client protein).

V. Detection of Hsp90 Levels

The level of Hsp90 in the plasma or serum, and in particular Hsp90α in the plasma or serum, may be detected by any suitable means. In particular, the level of Hsp90 may be determined by assaying for Hsp90 protein levels, although in alternative embodiments the level is determined by mRNA levels, or both.

A. Detection of Hsp90 Protein Levels

As will be appreciated by those skilled in the art, any means for specifically identifying and determining quantitatively the amount or concentration of Hsp90α polypeptide from a sample of plasma, serum or other non-cellular body fluid is considered. A particular method for detecting Hsp90α polypeptide in a sample is by means of using antibodies. Hsp90 antibodies have been prepared and are used by the skilled artisan. Antibodies directed towards Hsp90 polypeptide recognize both Hsp90α and Hsp90β isoforms. In a preferred embodiment, the method of detecting the presence of Hsp90α in serum or plasma is performed using antibodies that bind specifically to the Hsp90α isoform. In an alternative embodiment, the method of detecting the presence of Hsp90β in serum or plasma is performed using antibodies that bind specifically to the Hsp90β isoform. Polyclonal and monoclonal antibodies that are specific to Hsp90, Hsp90α and Hsp90β have been prepared and are used by the skilled artisan.

A variety of assays are available for detecting polypeptides with a labeled antibody. In a two-step assay, the immobilized Hsp90α molecule is incubated with an unlabeled antibody. The unlabeled antibody is then bound to a second labeled antibody that is specific for the unlabeled antibody. Unbound molecules are washed away and the presence of the label is detected. In a one-step assay, the Hsp90α molecule, if present, is immobilized and incubated with labeled antibody. The labeled antibody binds to the immobilized target molecule. Unbound molecules are washed away, and the presence of the label is detected. The choice of label on the antibodies may be radioactive atoms, a colorimetric tag, a fluorescent or chromophoric moiety, or an enzyme. Some examples of radioactive atoms are $^{32}P$, $^{125}I$, and $^3H$. Some examples of enzymes include horseradish peroxidase, alkaline phosphatase, and beta-galactosidase. An Enzyme Liked ImmunoSorbent Assay (ELISA) allows detection of an enzyme-complex with a substrate that produces a detectable product. Some examples of a fluorescent moiety include rhodamine and fluorescein.

In particular embodiments, an increase in Hsp90α that is detected is at least or at least about 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 40-, 41-, 42-, 43-, 44-, 45-, 46-, 47-, 48-, 49-, or 50-fold or more in relative and/or absolute concentration of Hsp90α when compared to a known reference amount, such as what was taken from the same individual prior to administration of an Hsp90-interacting drug, for example. In an alternate embodiment, an increase in Hsp90α is at least or at least about 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 40-, 41-, 42-, 43-, 44-, 45-, 46-, 47-, 48-, 49-, 50-fold or more in relative and/or absolute concentration of Hsp90α when compared to a known reference amount, such as what was taken from an individual not administered an Hsp90-interacting drug, for example.

B. Detection of Hsp90 mRNA Levels

The detection of Hsp90α mRNA in a sample of plasma or serum from an individual that has cancer or is suspected of having cancer or that needs Hsp90-interacting therapy can be determined by methods comprising Northern blot analysis, reverse-transcriptase PCR, or real-time reverse transcriptase PCR. The mRNA may be obtained from cancer cells, including tumor cells.

VI. Hsp90-Associated Molecules

In certain embodiments of the invention, the level of a molecule that is associated with Hsp90, such as by interacting directly or indirectly with Hsp90 (for example in a complex), is determined. In particular embodiments of the invention, a molecule that interacts with Hsp90 is a molecule that binds directly to Hsp90. In specific embodiments, the molecule binds to the Hsp90α isoform, although in alternative embodiments the molecule binds to the Hsp90β form, or to both isoforms. In further specific embodiments, the interaction between Hsp90 and the Hsp90-interacting molecule occurs as a direct or indirect result of cancer.

Exemplary Hsp90-associated molecules include co-chaperone molecules, such as Hop40, Hsp70, p50 and p23. Hsp90-associated molecules include hormone receptors, such as estrogen receptor (ER), progesterone receptor (PR), or glucocorticoide receptor (GR) (Pratt and Toft, 2003), for example. Other Hsp90-associated molecules include oncogene products (e.g. c-erbB2, bcr-abl, npm-alk, c-raf, v-src), regulators of cancer cell growth and cell cycle progression (e.g. cdk4, EGF-R, IGF1-R, telomerase), and apoptosis-related signaling (e.g., akt, mutant p53), for example.

Exemplary Hsp90-interacting molecules include one or more of the following: extracellular proteins including MMP2, VEGF, uPA, IGFI//II, IGFBP1-6, IGFBP-rP1-5, TGF-beta, TNF-alpha, and EGF. In specific embodiments, the Hsp90α interacting molecule may be an Hsp90 co-chaperone protein, such as Hsp Organizing Protein (HOP) or p23.

In particular embodiments of the invention, instead of or in addition to determining Hsp90α plasma or serum levels for cancer diagnosis, prognosis, and/or responsiveness to cancer therapy, the plasma or serum level of an Hsp90-associated molecule is determined for cancer diagnosis, prognosis, and/or responsiveness to cancer therapy. The level of any Hsp90-associated molecule may be determined in this embodiment of the invention, as exemplified by the Examples herein for Hsp90α.

VII. Obtaining and Processing of Sample from Individual

In particular embodiments of the invention, a sample is obtained from an individual in which level of Hsp90, and in specific embodiments Hsp90α, is desired to be measured. In certain aspects, a sample is obtained prior to and subsequent to administration of an Hsp90-interacting therapy. The sample may be of any kind so long as it may be processed to obtain plasma and/or serum from which to measure the levels of Hsp90. In specific embodiments, a sample comprising blood is drawn from the individual, such as from a vein, for example, and plasma and/or serum are obtained upon standard processing steps in the art, including centrifugation, use of anti-clotting factors, and so forth. Exemplary clotting factors include sodium citrate, sodium heparin, and so forth.

In particular embodiments, a non-cellular fraction is isolated by centrifugation of a cell-comprising body fluid such as blood, or by other means known to the art such as, but not limited to, by passing the body fluid through a filter or otherwise size fractionating or density fractionation to separate the body fluid, whereby the cellular and non-cellular components of the body fluid are separated and the non-cellular fraction is isolated. In preferred embodiments, plasma is isolated from whole blood through centrifugation. Serum can be further obtained by removing clotting factors such as fibrin thereby allowing blood to clot. In particular embodiments, either fresh (i.e., not frozen at any time) plasma or serum samples, or frozen and subsequently thawed plasma or serum samples may be used.

VIII. Combinatory Diagnostic, Therapy Responsiveness, and/or Prognosis Embodiments In certain embodiments of the invention, the detection of plasma or serum levels of Hsp90α is used in conjunction with obtaining additional information concerning cancer diagnosis, therapy responsiveness, and/or prognosis.

A. Combinatory Diagnostic Embodiments

In conjunction with determining plasma or serum levels of Hsp90α, additional information may be obtained by biopsy or processing of another type of sample from the individual that has cancer or is suspected of having cancer, for example. The additional information may be of any suitable type, although in particular embodiments the additional information is provided by detection of a tumor marker and/or risk marker, for example. Tumor markers are compositions from tumor cells (or by other cells of the body in response to cancer) that can be found in the blood, in the urine, in the tumor tissue, or in other tissues, for example. It is known that different tumor markers are associated with different types of cancer, and levels of the same tumor marker can be altered in more than one type of cancer. In particular embodiments, tumor marker levels are detectable in individuals once their cancer is beyond early stage. Risk markers are markers that are a mutation or alteration in a particular gene, and some people have a greater chance of developing certain types of cancer because of the presence of the change. Tests for risk markers can facilitate the health care provider in estimation of a person's chance of developing a certain cancer. For example, prostate-specific antigen (PSA) levels are often used to screen men for prostate cancer; also, CA 125 may be used to screen women who have an increased risk for ovarian cancer. Finally, imaging embodiments may be employed, such as, for example, PET, CAT, or MRI.

B. Combinatory Therapy-Responsiveness Embodiments

In specific embodiments, confirmation or corroboration of levels of Hsp90 in relation to a certain therapy response is employed, such as by utilizing a different measurement or detection method. For example, one may combine the Hsp90 level of an individual with the presence of a particular mutation in a gene, such as, for example, BRCA1, EGF-R, or p53, or level of a tumor marker, such as PSA, CEA, IGFBP-3, IGFBP-2, or Her2 extracellular domain, Abl oncogene, erbB2 oncogene, or alteration in expression level thereof, for example.

C. Combinatory Prognosis Embodiments

In particular aspects of the invention, in addition to determining the plasma or serum level of Hsp90 for prognosis, one may also determine one or more other factors in the determination of prognosis for an individual. For example, the invention may be used in combination with other determinants to assist in identification of life expectancy, prediction for response to treatment, stage of the cancer, and so forth. Exemplary embodiments of other prognosis factors include levels of other molecules in the plasma or serum or other tissue, cells, and/or body fluids of the individual. The health care provider will recognize that the type of cancer of the individual or cancer suspected for the individual will determine which appropriate prognostic test or tests may be utilized. Furthermore, location of the cancer throughout the body, such as for example in the lymph nodes, will assist in determination of stage of the cancer. In cases where the cancer has metastasized to one or more particular organs, prognosis information may be determined.

IX. Correlation Between Hsp90 Level and Diagnostic, Therapy Responsiveness, and/or Prognosis Embodiments In certain embodiments of the invention, the plasma or serum level of Hsp90 is correlated with cancer diagnosis, progression, and/or response to a cancer therapy that comprises Hsp90-interacting therapy, and/or cancer prognosis. In specific embodiments, the plasma or serum level of Hsp90 is modulated in correlation with cancer diagnosis, response to a cancer therapy that comprises Hsp90-interacting therapy, and/or cancer prognosis. One of skill in the art recognizes that for different cancer types the level of Hsp90 may be interpreted differently for cancer diagnosis, response to a cancer therapy that comprises Hsp90-interacting therapy, and/or cancer prognosis. For example, in some types of cancer the plasma or serum level of Hsp90 may increase following administration of a Hsp90-interacting therapy, whereas in other types of cancer the plasma or serum level of Hsp90 may decrease or not change following administration of a Hsp90-interacting therapy. In an exemplary case, an absence of modulation of plasma or serum level of Hsp90 following administration of a Hsp90-interacting therapy is informative, such as determining that the therapy is either responsive or is not responsive.

In specific aspects, detecting the level of Hsp90, and in particular Hsp90α, is employed to determine responsiveness to a therapy. In particular, the responsiveness to the therapy is determined by an increase in the level of Hsp90, a decrease in the level of Hsp90, or no significant change in the level of Hsp90. The modulation of the level may be dependent upon the cancer of the individual and of the therapy being employed. For example, in an exemplary embodiment the plasma or serum level of Hsp90 is increased in response to an Hsp90-interacting therapy, and such an increase indicates that the cancer is responding to the therapy. In an alternative but exemplary embodiment, the plasma or serum level of Hsp90 is increased in response to an Hsp90-interacting therapy, and such an increase indicates that the cancer is not responding to the therapy.

In another example, in some types of cancer the plasma or serum level of Hsp90 may increase as a result of presence of cancer in an individual (over a level in the individual prior to onset of the cancer and/or a level in a non-cancerous tissue of the individual, for example) and may therefore be considered diagnostic, whereas in other types of cancer the plasma or serum level of Hsp90 may decrease or remain unchanged as a result of presence of cancer in an individual and may therefore also be considered diagnostic. In specific embodiments, the plasma or serum level of Hsp90 is unchanged compared to a plasma or serum level in a non-cancerous tissue of the individual, and such an absence of level change determines that the individual does not have cancer, for example.

In yet another example, in some types of cancer the plasma or serum level of Hsp90 may increase upon particular stages of cancer in an individual (over a plasma or serum level in the individual prior to onset of the cancer, over a plasma or serum level in the individual in a lower stage of the cancer, and/or over a plasma or serum level in a non-cancerous tissue of the individual, for example).

X. Kits of the Invention

In certain aspects of the invention there is a kit suitable for use in the invention. In particular aspects, the kit is used for determining Hsp90 level, including Hsp90α level. In specific aspects, the kit comprises one or more reagents for detecting level of Hsp90α from a sample, including a sample comprising blood. In further aspects, the kit further comprises an Hsp90α-interacting drug and/or a chemotherapeutic drug that is not a Hsp90α-interacting drug. For example, in the case wherein the level of Hsp90α determines that the cancer of an individual is not responding to therapy, the kit can further provide an alternative drug for the cancer. Exemplary alternative cancer drugs include at least one or more of the following: e.g. Velcade, Herceptin, Tarceva, Avastin, Nexavar, gemcitabine, paclitaxel, cisplatin, or doxorubicin. Exemplary cancer drugs may be identified on the World Wide Web at multiple sites, including the website for Chemocare.

In certain aspects of the invention, one or more of the following chemotherapeutics are employed in addition to an embodiment of the invention: 13-cis-Retinoic Acid, 2-CdA, 2-Chlorodeoxyadenosine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic acid, Alpha interferon, Altretamine, Amethopterin, Amifostine, Aminoglutethimide, Anagrelide, Anandron®, Anastrozole, Arabinosylcytosine, Ara-C, Aranesp ®, Aredia®, Arimidex®, Aromasin®, Arranon®, Arsenic trioxide, Asparaginase, ATRA, Avastin®, Azacitidine, BCG, BCNU, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine wafer, Casodex®, CC-5013, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine liposomal, Cytosar-U®, Cytoxan®, Dacarbazine, Dacogen, Dactinomycin, Darbepoetin alfa, Daunomycin, Daunorubicin, Daunorubicin hydrochloride, Daunorubicin liposomal, DaunoXome®, Decadron, Decitabine, Delta-Cortef®, Deltasone®, Denileukin diftitox, DepoCyt™, Dexamethasone, Dexamethasone acetate, Dexamethasone Sodium Phosphate, Dexasone, Dexrazoxane, DHAD, DIC, Diodex, Docetaxel, Doxil®, Doxorubicin, Doxorubicin liposomal, Droxia™, DTIC, DTIC-Dome®, Duralone®, Efudex®, Eligard™, Ellence™, Eloxatin™, Elspar®, Emcyt®, Epirubicin, Epoetin alfa, Erbitux™, Erlotinib, *Erwinia* L-asparaginase, Estramustine, Ethyol, Etopophos®, Etoposide, Etoposide Phosphate, Eulexin®, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar®, Gleevec™, Gliadel wafer, GM-CSF, Goserelin, granulocyte-colony stimulating factor, Granulocyte macrophage colony stimulating factor, Halotestin, Herceptin, Hexadrol, Hexylen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG conjugate), Interleukin-2, Interleukin-11, Intron A® (interferon alfa-2b), Iressa ®, Irinotecan, Isotretinoin, Kidrolase, Lanacort, L-asparaginase, LCR, Lenalidomide, Letrozole, Leucovorin, Leukeran, Leukine, Leuprolide, Leurocristine, Leustatin, Liposomal Ara-C, Liquid Pred, Lomustine, L-PAM, L-Sarcolysin, Lupron, Lupron Depot®, Matulane, Maxidex, Mechlorethamine, Mechlorethamine Hydrochloride, Medralone, Medrol®, Megace, Megestrol, Megestrol Acetate, Melphalan, Mercaptopurine, Mesna, Mesnex, Methotrexate, Methotrexate Sodium, Methylprednisolone, Meticorten, Mitomycin, Mitomycin-C, Mitoxantrone, M-Prednisol, MTC, MTX, Mustargen, Mustine, Mutamycin, Myleran, Mylocel, Mylotarg, Navelbine®, Nelarabine, Neosar, Neulasta, Neumega, Neupogen®, Nexavar®, Nilandron, Nilutamide, Nipent®, Nitrogen Mustard, Novaldex, Novantrone, Octreotide, Octreotide acetate, Oncospar, Oncovin (t), Ontak, Onxal, Oprevelkin, Oraprod, Orasone, Oxaliplatin, Paclitaxel, Paclitaxel Protein-bound, Pamidronate, Panretin, Paraplatin, Pediapred, PEG Interferon, Pegaspargase, Pegfilgrastim, PEG-INTRON (t), PEG-L-asparaginase, PEMETREXED, Pentostatin, Phenylalanine Mustard, Platinol, Platinol-AQ, Prednisolone, Prednisone, Prelone, Procarbazine, PROCRIT®, Proleukin, Prolifeprospan 20 with Carmustine implant, Purinethol ®, Raloxifene, Revlimid®, Rheumatrex, Rituxan, Rituximab, Roferon-A® (interferon alfa-2a), Rubex, Rubidomycin hydrochloride, Sandostatin®, Sandostatin LAR, Sargramostim, Solu-Cortef, Solu-Medrol, Sorafenib, STI-571, Streptozocin, SU11248, Sunitinib, Sutent®, Tamoxifen, Tarceva®, Targretin, Taxol®, Taxotere®, Temodar®, Temozolomide, Teniposide, TESPA, Thalidomide, Thalomid®, TheraCys, Thioguanine, Thioguanine Tabloid ®, Thiophosphoamide, Thioplex, Thiotepa, TICE®, Toposar, Topotecan, Toremifene, Tositumomab, Trastuzumab, Tretinoin, Trexall, Trisenox, TSPA, VCR, Velban, Velcade®, VePesid, Vesanoid, Viadur, Vidaza, Vinblastine, Vinblastine Sulfate, Vincasar Pfs, Vincristine, Vinorelbine, Vinorelbine tartrate, VLB, VM-26, VP-16, Vumon, Xeloda®, Zanosar, Zevalin ™, Zinecard, Zoladex®, Zoledronic acid, and Zometa®, for example.

Reagents that are suited for detecting level of Hsp90α may be of any suitable kind, although in specific embodiments the reagents comprise antibodies to Hsp90 (α and/or β form); one or more primers to Hsp90α polynucleotide sequences; and/or one or more primers to polynucleotides that encode a polypeptide that interacts with Hsp90α, such as Hsp90-beta, Hsp70, CHIP, or c-raf, for example. Reagents that are suited for obtaining blood or plasma or serum from an individual may be included in a kit of the invention, such as a syringe, collection vial, needle, and so forth.

The kits may comprise a suitably aliquoted composition and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition, additional agent, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In this case, the container means may itself be a syringe, pipette, and/or other such like apparatus, from which the formulation may be applied to an infected area of the body, injected into an animal, and/or even applied to and/or mixed with the other components of the kit.

However, in other embodiments the components of the kit may be provided as dried powder(s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the composition is placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained. Irrespective of the number and/or type of containers, the kits of the invention may also comprise, and/or be packaged with, an instrument for assisting with the injection/administration and/or placement of the composition within the body of an animal. Such an instrument may be a syringe, pipette, forceps, and/or any such medically approved delivery vehicle.

XI. Examples

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Influence of Geldanamycins on Hsp90 Expression in Tumor Cells

When Hsp90 is bound to 17AAG or 17DMAG, expected results are an increase in co-chaperone expression (e.g. Hsp70) and a decrease in client protein levels. The loss of client proteins is due to rapid degradation of improperly folded molecules, and this has been demonstrated in preclinical models by us (Burger et al., 2004; Smith et al., 2005; Kaur et al., 2004) and/or clinical samples by others (Nimmanapalli et al., 2001; Munster et al., 2001; Solit et al., 2002; Eiseman et al., 2005; Grem et al., 2005; Benerji et al., 2005; Ramanathan et al., 2005; Matthew et al., 2005).

Figure 6:
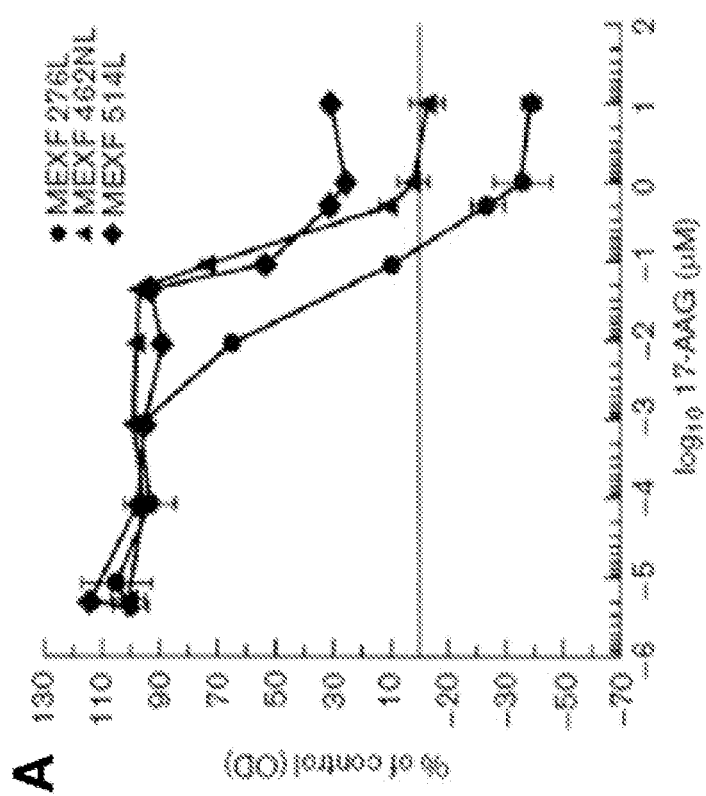
FIG. 6A demonstrates activity of 17AAG in three melanoma cell lines and comparison of Hsp90, Hsp70 (72) and/or c-raf client protein expression in the 17AAG sensitive melanoma cell line MEXF276L (FIG. 6B), and the 17AAG resistant cell line MEXF514L (FIG. 6C). Cells were treated at the respective concentrations that cause total growth inhibition (TGI) (Burger et al., 2005).
FIG. 6D illustrates immunofluorescence staining for Hsp90 isoforms a (red TRITC) and β (green FITC), and time course of their localization in presence and absence of 17AAG in drug sensitive MEXF276L cells. Co-localization of proteins results in the occurrence of orange to yellow colors in merged pictures. Bar=15 μm.
Figure 6:
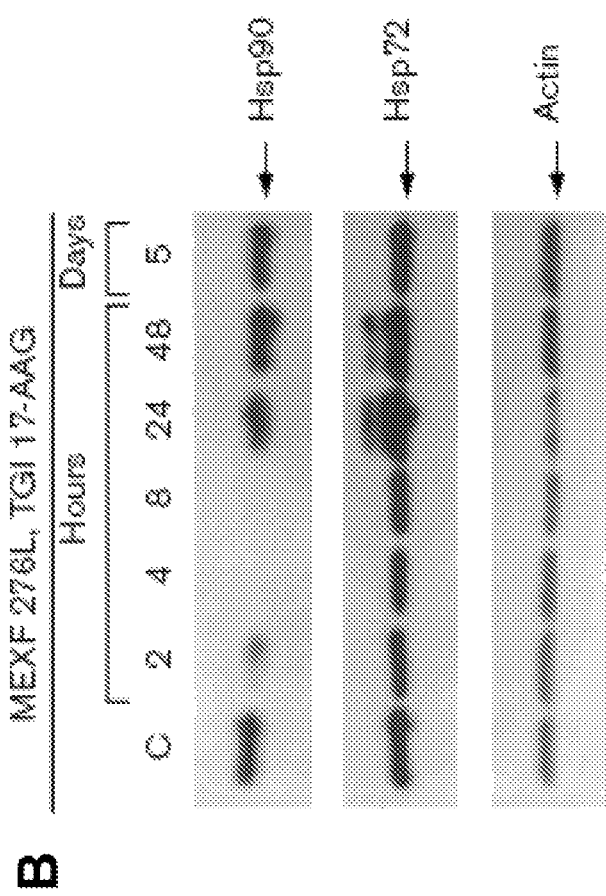
Figure 6:
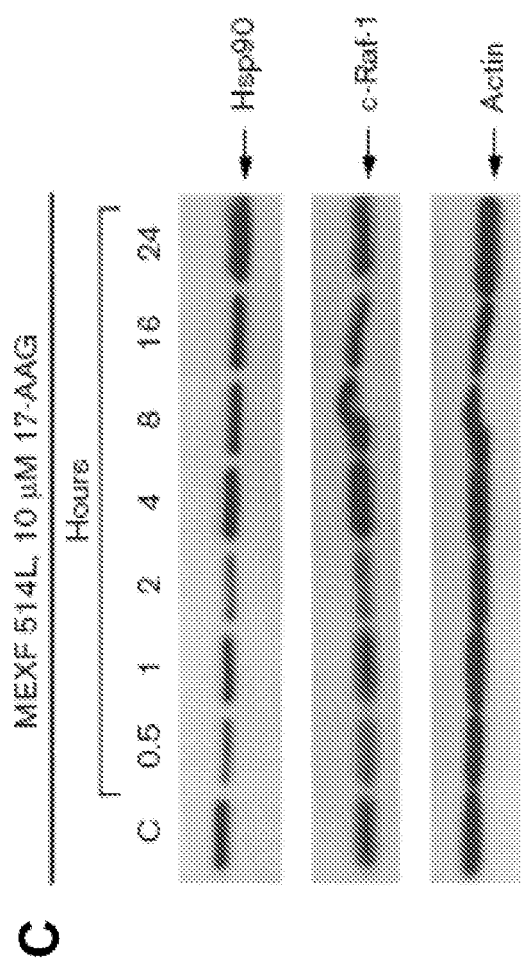
Figure 6:
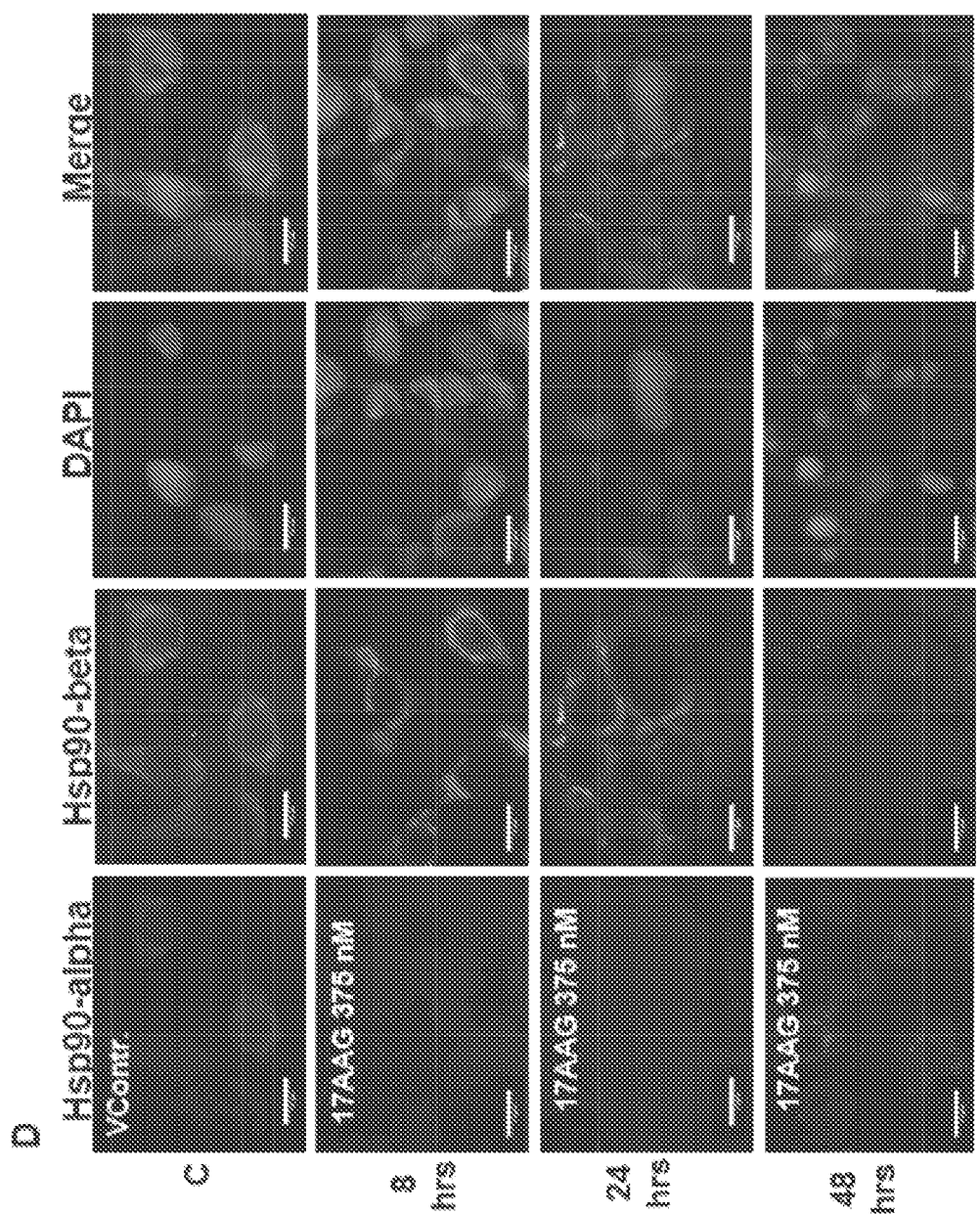

However, few studies have included the evaluation of direct effects of geldanamycins on their target Hsp90 (Burger et al., 2004; Smith et al., 2005; Eiseman et al., 2005; Ramanathan et al., 2005; Matthew et al., 2005). The inventors were the first to show that Hsp90 levels are modulated by 17AAG (Burger et al., 2004; Smith et al., 2005) (FIGS. 6A-6B) and that a loss of cytoplasmic Hsp90 occurs in 17AAG responsive, but not resistant tumor cells (FIG. 6B-6C) (Burger et al., 2004; Smith et al., 2005). The cell lines used in these studies were the geldanamycin sensitive melanoma cell line MEXF276L and the "resistant" cell line MEXF514L (FIG. 6A-6C) (Burger et al., 2005).

These in vitro observations were confirmed in tumor tissues of MEXF276 and MEXF514 xenograft models in vivo; cytoplasmic Hsp90 was down-regulated starting at 48 hours after treatment in responsive MEXF276 xenografts (Burger et al., 2004). Most recently, when it became evident that the α-isoform of Hsp90 is found secreted into the extracellular environment (Picard, 2004; Eustace et al., 2004), the embodiment that loss of cytosolic Hsp90 (FIG. 2B) in MEXF 276L cells is due to an enhanced secretion of Hsp90α into the tissue culture supernatant was explored. Hence, the inventors performed Hsp90 localization studies by using immunofluorescence imaging (FIG. 2D).

Figure 2:
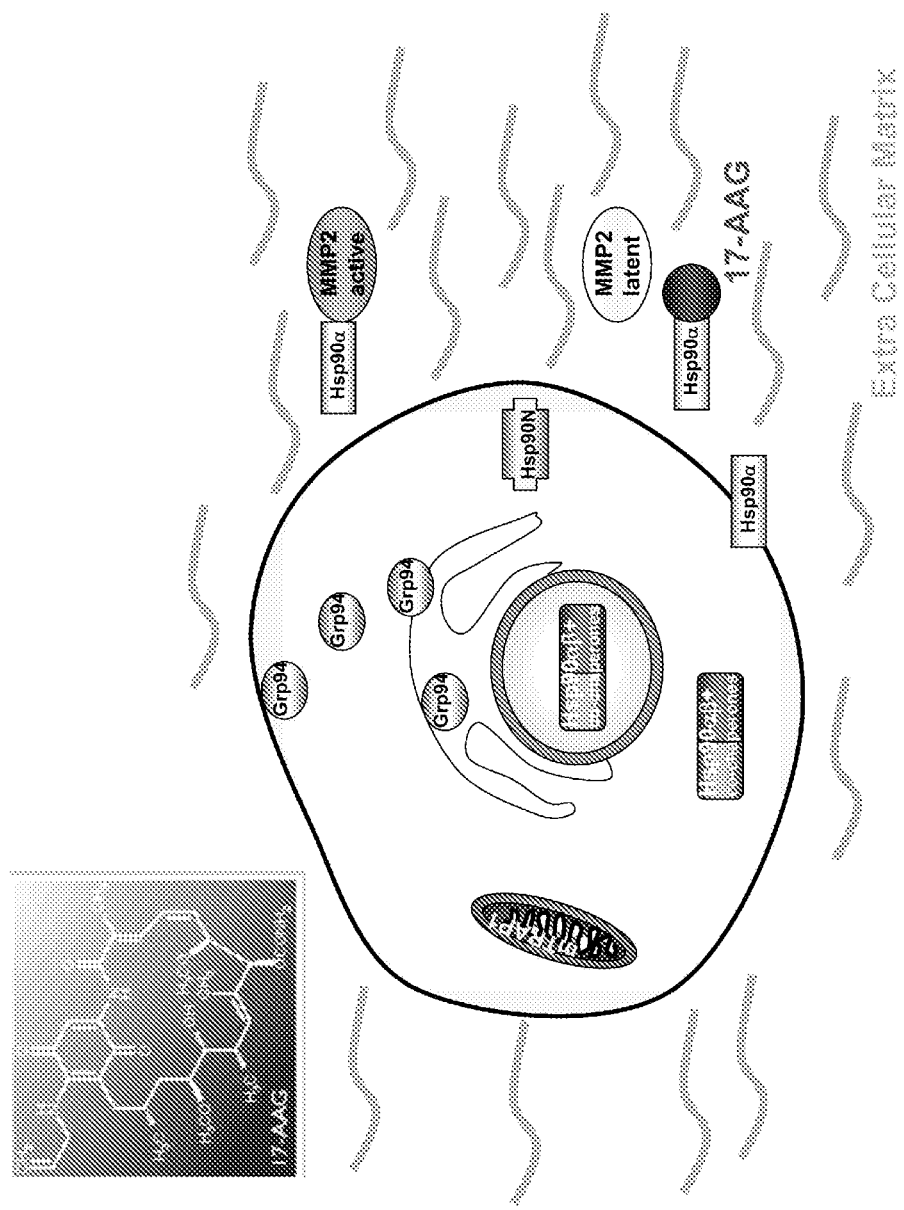
FIG. 2 shows cellular localization of exemplary Hsp90 family members. mTRAP1 is localized to the mitochondria, while GRP94 has a partial localization in the endoplasmatic reticulum and can present antigens on the cell surface. Hsp90α exists in the cytoplasm and can be secreted, while Hsp90β is only found within the cell. Hsp90N is a truncated from of Hsp90 lacking the N-terminal ATP and thus geldanamycin binding site. (adopted from Picard, 2004).

The latter revealed that Hsp90α and β co-localize in control MEXF276L cells, but that Hsp90α is lost at 2-24 hrs in sensitive melanoma cells that are exposed to 17AAG, whereas Hsp90β continues to reside in the cytoplasm (FIG. 2D).

Interestingly, melanomas are one of a very limited number of tumors that showed marked stabilization of disease in response to the geldanamycin analog 17AAG in the clinic (Banerji et al., 2005). Egorin and co-workers reported similar results relating to an observed down-regulation of Hsp90 for studies with 17DMAG in MDA-MB-231 breast cancer xenograft tissues (Eiseman et al., 2005). Therefore, in exemplary embodiments melanoma and breast cancer cell lines and xenografs thereof may be used in further studies.

Example 2

Secretion of Hsp90α-Influence of 17AAG

To confirm that an intra cellular decrease of Hsp90α is associated with a specific increase of secretion of Hsp90α into the extracellular milieu, the baseline of Hsp90 isoform expression and "total" (dimeric) Hsp90 was first examined. Whole cell lysates (WCL) and serum-free, conditioned medium (SFM) from the 17AAG-sensitive melanoma cell line MEXF276L (FIG. 3A-3B) were used.

In addition, levels of matrix metalloprotease 2 (MMP2, FIG. 3B), an extracellular client protein of Hsp90α were analyzed. In both, WCL and SFM, Hsp90 is readily expressed when detected with a monoclonal antibody that does not discriminate against the isoform α/β (anti-total Hsp90 from BD (Burger et al., 2005; Smith et al., 2005) (FIG. 3A-3B). Hsp90α, detected with an isoform-specific polyclonal antibody (Stressgen), is also seen in WCL and SFM. In contrast, Hsp90β (isoform-specific monoclonal antibody, Stressgen) is only found within the cell. This is consistent with data shown in FIG. 6D. MMP2 in its active and latent form is detectable in SFM (FIG. 3B), but not in lysates (data not shown). An unexpected finding is that treatment of these cells over 8-24 hrs with 17AAG, under conditions where the cells are not undergoing apoptosis (FIG. 3C-3D), there is an increased detection of Hsp90α but not Hsp90β in the medium, and moreover, this is accompanied by a shift of the extracellular localized MMP2 from the fully active 66 kd form to the 72 kd latent form (FIG. 3C). These data are concordant with the observations of Eustace et al. that the Hsp90α is the "secreted" isoform and is required to fold MMP2 into an active form (Eustace et al., 2004).

Example 3

Hsp90α Detection in Human Patient Plasma

Figure 4:
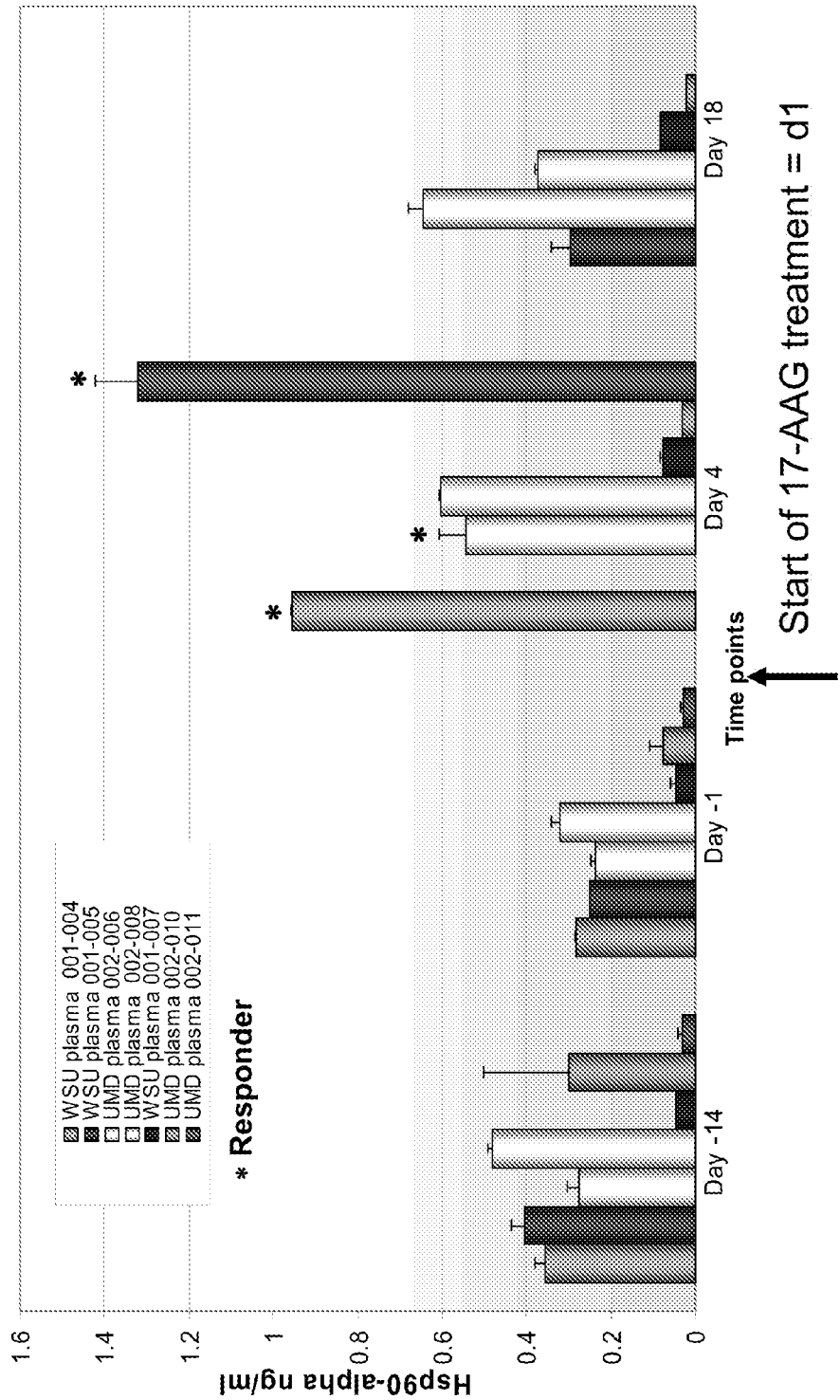
FIG. 4 shows Hsp90α levels determined by quantitative StressXpress ELISA in plasma from cancer patients before and after treatment with 17AAG. Day −14 represents plasma Hsp90α in cancer patients prior to therapy. Day −1 show the Hsp90α levels after sorafenib treatment and before 17AAG. Day 4 is 72 hours after 17AAG and day 18 is 72 hours after the third cycle of 17AAG. Not all patients received a 3rd cycle. Data are presented as mean Hsp90α concentration and ng/mL±standard deviation. Asterisks indicates response to 17AAG.

The results described above indicate that as a function of geldanamycin action on tumor cells, secretion of Hsp90α but not Hsp90β might be utilized as a pharmacodynamic marker of drug action. Sorafenib (BAY43-9006) is a reversible ATP-site-directed protein kinase inhibitor that was initially of interest owing to its action as a raf kinase antagonist. However, further characterization of the molecule has revealed that it has potent activity against VEGF-Receptor isoforms. It has recently been approved for single agent use in renal cell carcinoma, owing to valuable evidence of disease stabilization (Strumberg, 2005). It was of great interest to combine sorafenib with BAs, since multiple investigators were previously able to demonstrate that both 17AAG and 17DMAG prominently down-regulate craft (Burger et al., 2004; Smith et al., 2005; Hollingshead et al., 2005; Kaur et al., 2004; Nimmanapalli et al., 2001; Munster et al., 2001; Soli et al., 2002; Eiseman et al., 2005; Grem et al., 2005; Banerji et al., 2005; Ramanathan et al., 2005; Matthew et al., 2005), and it has also been shown that both BAs are potent inhibitors of VEGF signaling in endothelial cells with abundant evidence of preclinical anti-angiogenic activity (Kaur et al., 2004). Blood was taken from patients before treatment on day −14, then on day −1 two weeks after daily oral sorafenib; followed by blood collections of day 4 and day 18, which was in both instances 72 hrs after the initial and a third dose of 17AAG respectively (FIG. 4). Patient plasma from this phase I study was available and approved for use in studies of 17AAG pharmacodynamic effects and thus, the samples were assayed for presence of circulating Hsp90α by employing the StressXpress Hsp90α ELISA kit (Stressgen). The Hsp90α ELISA is a sandwich immunoassay that contains a recombinant Hsp90α standard which is used to generate a standard curve and enable quantitative measurements in g/mL (assay specificity 50 pg/mL). It is specific for Hsp90α and does not cross react with Hsp90β, Grp94, Hsp60 or Hsp70. The assay has been certified for detection of human Hsp90α in biological samples including plasma (Stressgen product information). FIG. 4 demonstrates that in the 7 patients studied, there was little difference in plasma Hsp90α detected at baseline and after the 14 day "run in" period of sorafenib alone. However in 3 of 7 patients there was an increase in Hsp90α detectable on day four after administration of the first 17AAG dose (indicated by asterix). Of these patients, two had evidence of a "minor" response four weeks later; and while one additional patient who had also a noteworthy increase by day 4 in plasma Hsp90α did not complete treatment owing to complications from a concomitant illness, radiographic studies at the time he came off study indicated changes consistent with tumor necrosis (FIG. 4).

Example 4

Proteomic Analysis and Verification of Hsp90 Immuno-Complexes

In order to verify the specificity of antibodies used in initial studies for detection of Hsp90 isoforms and to demonstrate our capability to perform Hsp90-complex analyses, the composition of immuno-precipitates with Hsp90 antibodies from cancer cell lines were examined (Table 1). Whole cell lysates were prepared from the exponentially growing MV411 human leukemia cells and Hs578Ti8 breast cancer cells, and 250-500 μg of total cellular protein was incubated with either anti-Hsp90α (Stressgen) or an anti-Hsp90 antibody that recognizes both isoforms (from BD) (Table 1).

| Antibody used for Immunoprecipitation (IP) | Cell Line WCL (tumor type) | Detected Hsp90 isoform in IP | Coverage | # Peptide fragments | Score (range) |
|---|---|---|---|---|---|
| Anti-Hsp90α (Stressgen): detects Hsp90α from human, mouse, rat and other species; does not cross react with Hsp90β | MV411 (leukemia) | Hsp90α<br>Hsp90β | 13.5%<br>24.4% | 9<br>14 | 3.77-2.62<br>5.57-1.49 |
| Anti-Hsp90 (BD Biosciences): detects both Hsp90α and β from human, mouse, rat and other species | MV411 (leukemia)<br>Hs578Ti8 (breast) | Hsp90α<br>Hsp90β<br>Hsp90α<br>Hsp90β | 15.3%<br>24.9%<br>11.9%<br>15.3% | 12<br>12<br>9<br>8 | 4.97-2.12<br>2.3-1.94<br>4.33-0.91<br>1.76-1.36 |

Immuno-complexes were adsorbed onto sepharose A-agarose beads and washed extensively with cell lysis buffer. IPs were then subjected to SDS-Page electrophoresis on 4-20% tris-glycine gradient gels and stained with Proteomic blue (Proteome Systems). Bands were cut from 85-95 kD and digested with trypsin. Mass spectra were obtained with an LCQ Deca XP ion trap mass spectrometer equipped with an on-line microcapillary HPLC (ThermoElecton, San Jose, Calif.) using two C18 peptide captraps (Michrom BioResources Inc., Auburn Calif.) and one PicoFrit C18, 15 micron tip column (New Objective, Woburn Mass.) for high throughput. For protein identification, MS/MS spectra were compared against databases using Sequest software.

In both cases, IP with anti-Hsp90α and total Hsp90 antibodies, and in all cell lines studied, the peptides with highest coverage and highest number of fragments were identified by the Sequest software as Hsp90α and Hsp90β respectively (Table 1). In addition, for Hsp90 isoforms, significant scores (>2.5) were obtained.

However, other proteins, among those known Hsp90 clients, were also detected but at low coverage. Thus, the proteomic analysis of immuno-complexes with the Hsp90 antibodies used in our studies show that they detect Hsp90 and that in the cytoplasm Hsp90 exists as a dimer of its α and β isoform. More detailed analyses that include BA treated cell extracts and supernatants may be undertaken.

Example 5

Figure 5:
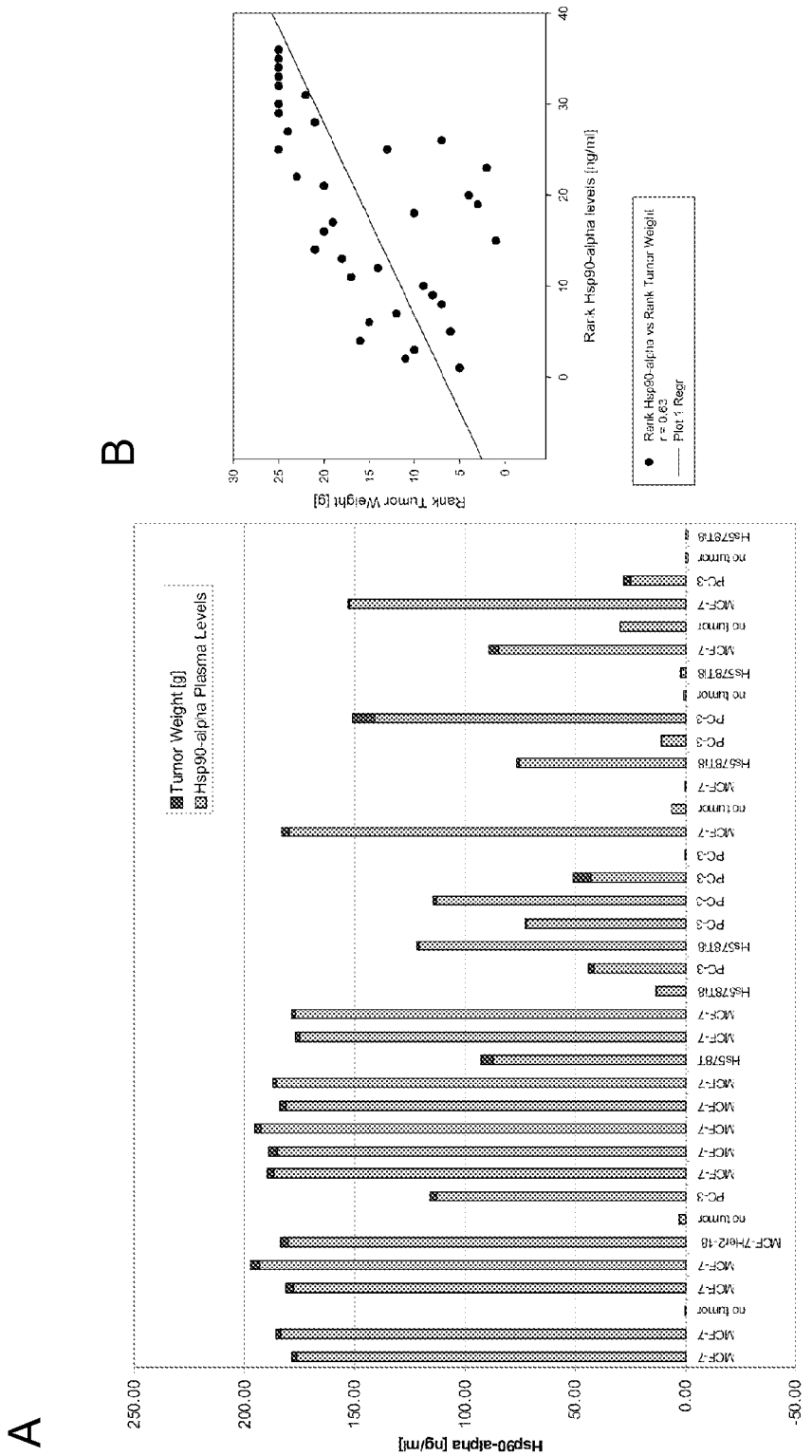
FIG. 5A shows Hsp90α levels in plasma from tumor-bearing nude mice (dark blue, blue, red bars) compared to animals with no tumor (black bars). Hsp90α concentrations were determined by ELISA assay as ng/mL (mean of two independent measurements).
FIG. 5B provides Spearman rank correlation and regression analysis comparing tumor weight in g to Hsp90α plasma levels in ng/mL, r=0.63 over all tumors.

Circulating Hsp90α as a Biomarker for Detection, Prediction and Measurement of Response to BAs in Preclinical Model Systems The experiments presented above in FIGS. 4 and 5 indicate that tumors in animals and people elaborate Hsp90α into their surrounding medium. Although the assay utilizes a Hsp90α-specific antibody and is certified by the manufacturer for use with human plasma and tissues, the exact identity of the molecule detected by the ELISA, its co-chaperones and binding proteins in the extracellular milieu, and the time course of its appearance in the medium may be established, and statistically significant numbers of samples may be analyzed. In specific embodiments of the invention, two exemplary "sensitive" animal models to BAs and two exemplary "resistant" models are assayed for further characterization of whether exposure to drug leads to an increase in secreted Hsp90α as a function of time and drug-induced inhibition of cell growth without occurrence of cell debris. Because it has been previously demonstrated that 17AAG and 17DMAG have identical modes of action, one BA may be utilized, namely 17AAG, for additional in vitro and xenograft studies.

Model Systems

The exemplary BA-responsive models MEXF276L (melanoma), MDA-MB-231 (breast), and the resistant models MEXF514L (melanoma), and Hs578Ti8 (breast) (FIG. 2A, FIG. 5) (Burger et al., 2005; Smith et al., 2005; Hollingshead et al., 2005; Eiseman et al., 2005; Price et al., 2005) may be utilized. In all four cases, the cancer cell lines grow well as monolayer on plastic in vitro and as xenografts in vivo. MEXF276L, MEXF514L (Burger et al., 2005; Smith et al., 2005), and MDA-MB-231 (Eiseman et al., 2005) have been used by the inventors before to study BA action and are well defined. Hs578Ti8 is a subclone of the Hs578T breast cancer cell line (from American Type Culture Collection). Parental Hs578T cells are little tumorigenic and have a very low take rate in nude mice. The Hs578Ti8 subclone was selected by passages and selection of invasive cell fractions of Hs578T through Boyden chambers. A total of 8 selection processes let to Hs578Ti8 (Hs578T invasive cells after 8 passages), which grow in nude mice with a take rate of 95%. MEXF276L and Hs578Ti8 secret MMP2 into conditioned media (Veerasamy et al., 2006; Fiebig and Burger, 2001). Hsp90α and β antibodies are used and the validated StressXpress Hsp90α ELISA from Stressgen (now Nventa), and total anti-Hsp90 antibodies (from BD Biosciences/Transduction Laboratories) are used, as in previous publications (Burger et al., 2005; Smith et al., 2005; Hollingshead et al., 2005; Kaur et al., 2004).

Animals

Female and male athymic nude mice (NCr nu/nu, 4-6 weeks old) may be utilized from the National Cancer Institute's Animal Production Facility, Frederick, Md. Drugs. 17AAG and 17DMAG may be purchased from InvivoGen, San Diego, Calif. Cisplatin, taxol, and dacarbacine may be obtained from Sigma and/or as clinical formulations from our hospital pharmacy.

Statistics

Statistical significance between experimental groups may be routinely assessed using ANOVA. Any direct comparison of values is performed using ANOVA and a Students t test with a p-value set at 0.05. In vivo data is evaluated as median relative tumor volume and statistically analyzed using the nonparametrical Wilcoxon Mann-Whitney test. The degree of variability of values for the median is assessed as 95% confidence intervals. For correlation analyses of continuous data the Pearson correlation, covariances, and sums of squares of deviations from the mean and sums of cross-products of deviations (SSCP) is determined. The usual probabilities and the Bonferroni adjustments are used with Pearson correlations. For rank-order data, correlations are performed with the Spearman's rho test. Statistical packages available include SPSS 2000 SigmaPlot and SYSTAT version 10, SYSTAT Software Inc., Chicago, Ill.

Example 6

The Specific Effect of Hsp90 Antagonists on Hsp90α Isoform Secretion into the Extracellular Compartment of Tumor Cells In Vitro (Medium) and in Nude Mice (Plasma) Bearing Human Tumor Xenografts In Vivo The specific effect of Hsp90 antagonists on Hsp90α isoform secretion into the extracellular compartment of tumor cells in vitro and in nude mice bearing human tumor xenografts in vivo.

In Vitro Cell Line Studies

Figure 3:
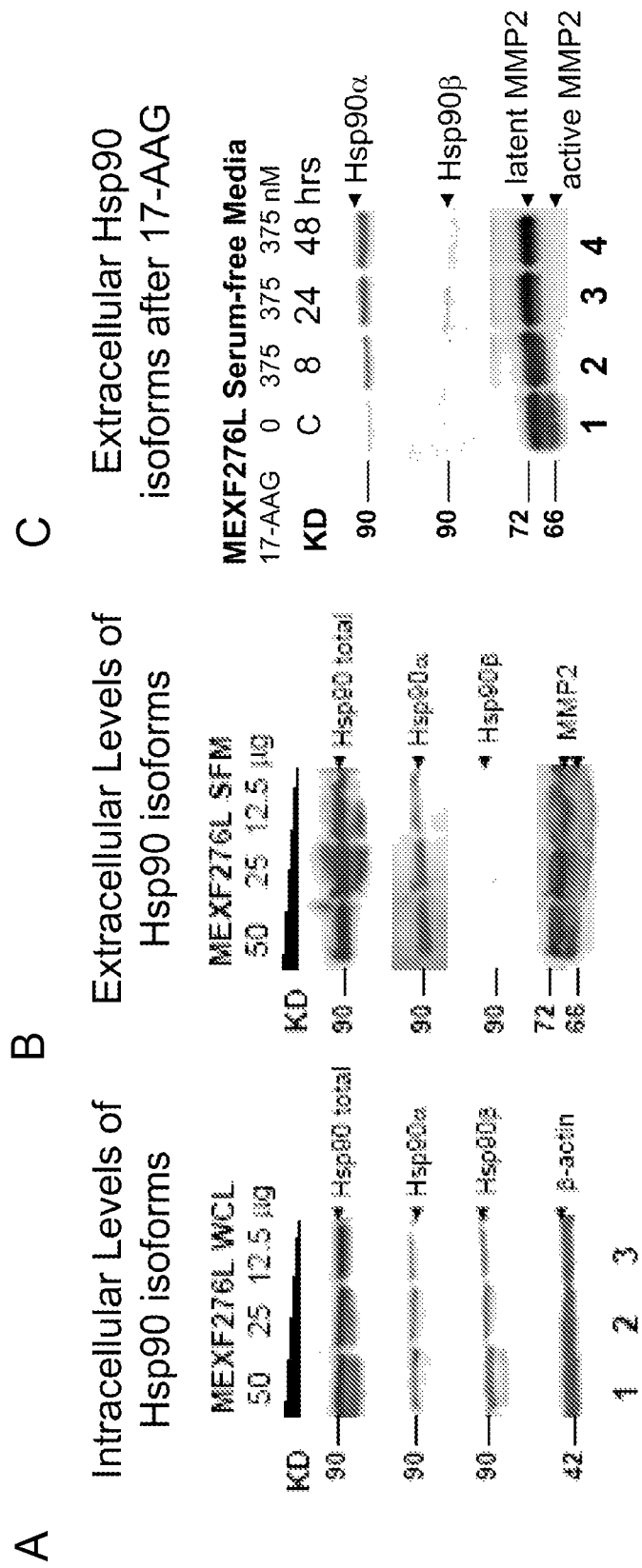
FIG. 3 demonstrates that Hsp90α but not Hsp90β are secreted into the extracellular environment and are modulated upon 17-AAG exposure.
Figure 3:
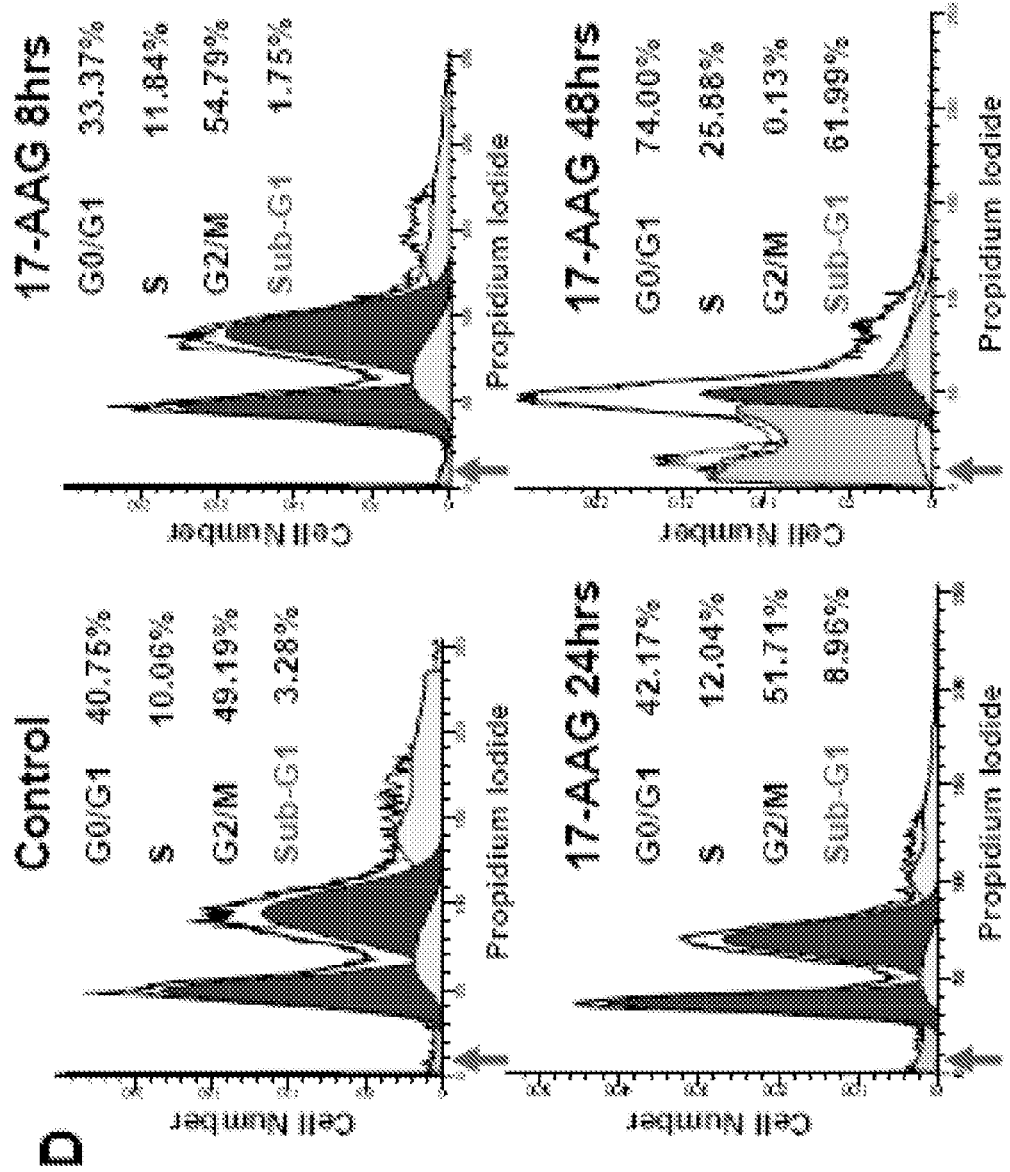

First, the concentration and time is determined of 17AAG and 17DMAG exposure causing cell death in the two pairs of BA sensitive and resistant cell lines described above by using the methyltetrazolium bromide (MTT) proliferation assay and flow cytometry (as in FIG. 3).

MTT Assay.

Although previously determined drug concentrations that inhibit the growth of the melanoma cell lines MEXF276L and MEXF514L to 50% (IC50) or 100% (IC100=total growth inhibition/TGI) are known (Burger et al., 2004; Smith et al., 2005), the latter studies employed the sulforhodamine B (SRB) assay and were limited to 2 day and 4 days of continuous exposure to 17AAG. Drug concentrations may be determined that are required to achieve IC50s and TGIs after 1, 2, 8, 24, 48 hours, and 5d of continuous exposure to drug in all four cell lines.

Briefly, two to three thousand cells are seeded in a volume of 0.1 ml into 96-well plates in complete media and cells allowed to attach overnight at 37° C./5% $CO_2$. For each cell line, a day 0 plate (cell growth at time of drug addition) is generated that allow determining total growth inhibition. Drugs are added in 0.1 ml of medium to obtain final drug concentrations between 0.0001 and 10 µM. Each drug concentration is plated in replicates of 8 wells and three independent experiments are performed. For shorter drug exposures including 1, 2, 8, 24 and 48 hrs drug is removed at the indicated time points and replaced by fresh growth medium. This allows one to examine reversibility of drug effects (concentration×time) and a more accurate prediction of concentration and duration of exposure needed for correlation to in vivo experiments and drug levels in patient plasma. Assays are developed after 5 days of incubation and are terminated by addition of MTT to the growth media. Effects are assessed by measuring reduction of MTT to purple formzan by viable cells that is extracted with DMSO; plates are then read at 550 nm using a Synergy™ HT Multi-Detection Microplate Reader and KC4 software (Bio-Tek, Winooski, Vt.). Growth inhibition is assessed as inhibitory concentration 50% and 100%/TGI compared to untreated and vehicle treated controls.

FACS (Fluorescence Activated Cell Sorting).

A flow cytometry apparatus is utilized to submit labeled cell suspensions of MEXF276L, MEXF514L, Hs578Ti8 and MDA-MB-231 that are treated with vehicle (control) and 17AAG or 17DMAG at their respective IC50 and IC100 concentrations at a given time point. 17DMAG however is only used to treat the sensitive cell lines MEXF276L and MDA-MB-231. Cells are also treated with 1 µM of the cytotoxic agent cisplatin for 24 hrs as a positive control for apoptosis. Labeling is done with propidium iodide and bromo-desoxyuridine (BrdU) by using the APO-BRDU™ BD Biosciences Pharmingen Apoptosis Detection Kit. This enables detection of DNA fragmentation, a process that results from the activation of endonucleases during apoptosis. Fragmented DNA utilizes a reaction catalyzed by exogenous deoxynucleotidyl transferase (TdT), referred to as "end-labeling" or "TUNEL" (terminal deoxynucleotidyl-transferase dUTP nick end labeling). TdT catalyzes a template-independent addition of BrdUtriphosphates to the 3'-hydroxyl (OH) termini of double- and single-stranded DNA. After incorporation, these sites are identified by flow cytometric means by staining the cells with a FITC-labeled anti-BrdU mAb. Cells are grown in 100×20 mm dishes and treated with 17AAG for 1, 2, 8, 24, and 48 hrs and than washed, fixed in alcohol and stained according to the protocol provided by the APO-BRDU™ kit. Data is analyzed as in FIG. 3 and the fraction of BrdU-positive as well as cells in sub-G1, G1, S, and G2/M phase determined. These studies are useful to further characterize that Hsp90α that is detected in serum-free medium as a function of drug dose is not merely reflecting cell death (see FIG. 3).

Preparation of Whole Cell Lysates and Supernatants for Western Blotting and Hsp90α ELISA.

Cell lines are treated at 17AAG and 17DMAG concentrations and time points described under FACS above. One may use 100 µM dacarbacine with the melanoma cell lines and 1 µM taxol with breast cancer lines, both at a 24 hrs exposure, as a control to demonstrate specific secretion of Hsp90α upon BA exposure. These drugs are standard therapies for respective tumor types in the clinic and these drugs may also be used as control for the proposed in vivo experiments. For collection of serum-free medium (SFM) and whole cell lysates (WCL), 2.5 million cells will be seeded in T75 flasks and allowed to grow to about 80% confluency (in RPMI1640, 10% FCS, 37° C./5% $CO_2$). First, cells are washed twice with phosphate buffered saline and once with serum-free RPMI1640. Then 10 ml of serum-free RPMI1640 medium is added and cells are incubated for 2 hrs. The latter medium is subsequently removed and replaced by fresh serum-free medium that contains drug. Supernatants are removed and concentrated; whole cell lysates are collected simultaneously. Cells are lysed by using the BIORAD Bio-Plex Cell Lysis kit. Supernatants (SFM) are concentrated using Centricon Plus-20 centrifuge filter devices by following the manufacturer's instructions. Protein content of lysates and supernatants are measured by using the Bradford assay (BIORAD).

Western Blotting.

Precast 4-20% Tris-glycine gradient gels may be obtained from Invitrogen, for example. Equal amounts of protein (12.5 µg of SFM and 25 µg of WCL respectively) are boiled in SDS loading buffer and separated for 2.5 hours at 125V. Proteins are then transferred onto Hybond P membranes (Amersham), and the expression levels of total Hsp90, Hsp90α, Hsp90β (all Stressgen), and MMP2 (Calbiochem) detected by using the ECL Western blotting kit (Amersham). Furthermore, Hsp70 expression, the expression of c-raf1, AKT, CDK4 and other client protein levels of interest are also characterized. Antibody concentrations and sources are used as described.

Hsp90α StressXpress ELISA.

Cell lysates and supernatants assayed by Western blotting will also be analyzed with the StressXpress Hsp90α ELISA kit and the results compared. We will use 50-500 ng protein per reaction as determined by us as the range of total protein from SFM and WCL that will produce measurements within the linear range of the Hsp90α standard curve. Recombinant Hsp90α standards (4 ng/ml, 2 ng/ml, 1 ng/ml, 0.5 ng/ml, 0.25 ng/ml, 0.125 ng/ml, 0.0625 ng/ml and 0 ng/ml) will be prepared and a standard curve generated for each set of samples. The StressXpress ELISA kit has been validated by the manufacturer for use with plasma and cell lysates to contain a low intra and inter-assay coefficient of variation (<10%) and high precision.

Antibody analysis may be performed with triplicate measurements per sample. The Hsp90α ELISA is based on a sandwich antibody methodology with one monoclonal Hsp90α antibody adsorbed to the assay plate and a second anti-Hsp90α antibody added that is conjugated the horseradish peroxidase. TMB (tetramethylbenzidine) is used as substrate and positive, yellow reactions are read at 450 nm with our Synergy™ HT Multi-Detection Microplate Reader and KC4 software (Bio-Tek, Winooski, Vt.).

In Vivo Xenograft Studies.

This embodiment focuses on elaborating previous results with in vivo model systems and to further investigate the embodiment that plasma Hsp90α correlates with mere tumor weight in mice. It is also evaluated whether an increase in plasma Hsp90α occurs in dose and time-dependent manner in animals bearing responsive (MEXF276, MDA-MB-231) versus xenografts that do not respond (MEXF514, Hs578Ti8) to BAs (17AAG) (Burger et al., 2004; Smith et al., 2005; Hollingshead et al., 2005; Kaur et al., 2004). Moreover, the specificity of enhanced plasma Hsp90α is examined for 17AAG response by comparing Hsp90α levels to those in mice that were treated with an effective standard cytotoxic drug.

Correlation Between Tumor Burden and Circulating Hsp90α.

Initial data shown in FIG. 5 indicate that circulating plasma Hsp90α correlates with tumor weight of xenografted human tumors in nude mice. Of three cell lines that were established as xenografts and tested for circulating Hsp90α levels, all showed plasma Hsp90α (MCF-7, Hs578Ti8, PC-3). However, the same tumor weight of MCF-7 produced more plasma Hsp90α than that of PC-3. Here, the studies are extended to the MEXF276L, MEXF514L and MDA-MB-231 models and to age-matched mice that are tumor-free. By reviewing the data shown in FIG. 5, one may calculate that the sample size (number of specimen, assuming one specimen per given time point) to detect a difference of 0.75 of a standard deviation between the cancer and non-cancer groups with a two-sided test on the Hsp90α level should be at least 29 specimen (5% significance level with 80% power). A multiple regression model is used to assess the difference of Hsp90α levels while adjusting for tumor size. One may therefore implant 60 female nude mice (age 6-8 weeks) with fragments derived from donor animals bearing MEXF276L (n=15), MEXF514L (n=15), MDA-MB-231 (n=15), and Hs578Ti8 (n=15) xenografts using engraftment techniques described before (Fiebig and Burger, 2001). A tumor fragment may be implanted in each flank of an animal. In addition, 15 mice from the same source and age are used as "normal" plasma control animals. The 15 mice of each tumor type are subdivided into five groups of 3 animals and sacrificed at subgroups of 3 at times when tumors reach a mean average weight of 75 mg, 250 mg, 500 mg, 1 g, and 1.5 g respectively. Tumor weight is determined by bi-weekly measurements of width and length of tumors with an electronic caliper and processing of these data with our LABCAT Tumor Tracking & Measurement Software version 8.0 (Innovative Programming Associates Inc., N.J.).

Blood and Tissue Collection.

Mice are euthanized using $CO_2$ (carbon dioxide) asphyxiation followed by cervical dislocation and blood collected from the axillary vessels post mortem into heparinized syringes (Braun). Mouse blood is transferred into heparinized 2.0 ml Eppendorf tubes and centrifuged for 10 min. at 2,700 g. Plasma is collected and stored in a −80° C. freezer. Tumor tissues are excised from the tumor-bearing animals, freed from potential core necrosis and cut in small pieces followed by flash freezing in liquid nitrogen.

Influence of 17AAG Versus Standard Cytotoxic Agents on Circulating Hsp90α Levels.

17AAG response and efficacy studies with melanoma and breast cancer xenografts are essentially performed as described in previously published work (Burger et al., 2005; Hollingshead et al., 2005). In brief, 5×5 mm tumor fragments are implanted subcutaneously into 40 female nude mice (6-8 weeks; one tumor/flank) and their growth monitored by biweekly serial caliper measurement using the LABCAT Tumor Tracking & Measurement system (Burger et al., 2005; Hollingshead et al., 2005; Fiebig et al., 2001).

When tumors reach a size between 100-250 mm$^3$ [mg], one may randomly distribute the animals into a control and two treatment groups (n=12 animals/group or more depending on number of animals that fulfill randomization criteria). One of the treatment groups may receive the BA 17AAG, the other the clinically used standard cytotoxic agent.

Drugs, Doses and Schedules.

17AAG is formulated in 10% DMSO in PBS and administered to mice intra peritoneally (i.p.) at 60 mg/kg/day on days 1-5, and 8-12 (Burger et al., 2004). This dose, if administered on days 1-5, and 8-12 after randomization has previously shown to be well tolerated (no animal death) and caused significant growth inhibition of 92% compared to control in the MEXF276 xenograft model. Actual tumor remissions were seen between days 10-17 of the experiment. In the case of the melanoma xenograft models one may use dacarbacine (DTIC) as a standard agent and for the breast cancer models one may use taxol. Taxol (20 mg/kg/d on days 1, 8, 15 i.v.) and DTIC (70 mg/kg/d on days 1-4, 15-18 i.p.) is administered at their respective maximal tolerated doses in nude mice as established previously (Fiebig and Burger, 2001). Each of the 3 experimental groups are subdivided into 4 groups of 3 animals from which blood and tumor tissue are collected 72 hours (day 4) after start of treatment (identical to a current 17AAG clinical protocol), on day 8 (before the second cycle of 17AAG), on day 11 (72 hours after the second cycle of 17AAG) and on day 15 (time of optimal 17AAG effects on tumor growth in previous efficacy experiments (Burger et al., 2005). Blood and tumor tissue is collected and processed as above.

Hsp90α StressXpress ELISA.

The Hsp90α ELISA assay as described in detail elsewhere herein is performed in triplicate for each plasma specimen and with all lysates from tumor tissues collected in the two nude mouse studies described above. Lysates are assayed at 500 ng protein and plasma samples diluted 1:25 v/v with sample diluent provided with the StressXpress kit. A dilution of 1:25 was found optimal for assaying Hsp90α in mouse and human plasma. The assays are performed as outlined elsewhere herein.

In specific embodiments, the studies described above further characterize the use of secretion of Hsp90α to serve as a marker of BA action to cause an antiproliferative effect in vitro and in vivo, and the specificity of this action.

Example 7

Identification of Hsp90α-Associated Molecules in the Extracellular Compartment of Tumor Cells In Vitro and In Vivo The present example concerns identification of Hsp90α-associated molecules in the extracellular compartment of tumor cells in vivo (serum-free medium) and in animals (plasma) bearing human tumor xenografts in vivo, such as by utilizing proteomic techniques, for example.

Hsp90 Complexes in Serum-Free Medium from Cell Lines

Control (basal level) tissue culture supernatants are utilized that are generated with SFM from each of the melanoma and breast cancer model systems (n=4) to perform immunoprecipitations (IP) with antibodies against the Hsp90α isoform and "bulk/total" Hsp90. Hsp90 complexes are precipitated from concentrated supernatants (100 μg total protein as per Bradford assay) with the antibodies (2 μg per IP) and are then incubated over night at 4° C. The resulting immuno-complexes are adsorbed onto sepharose A beads and washed as described above. Three independent IPs are performed from SFM of each of the 4 cell lines per antibody.

Hsp90 Complexes in Plasma from Tumor-Bearing Mice

The detection of biomarkers in plasma by proteomic technologies presents a challenge owing to the presence of high-abundance proteins such as albumin, immunoglobulins, transferrin and fibrinogen. Twenty-two of the most abundant proteins make up 99% of the total protein mass in plasma. In order to be able to analyze Hsp90 antibody complexes in mouse plasma, one may employ the ProteoPrep® 20 Plasma Immunodepletion kit (Sigma), which removes 20 high abundance proteins (>98% of total protein). Thus, 100 μL of plasma that was pooled from 3 animals of each xenograft model and was shown to contain high Hsp90α levels by ELISA assay as described elsewhere herein are depleted using a 3.7-mL prototype spin column by following the ProteoPrep instruction manual. Three independent plasma IPs are performed for each tumor model from 100 μL depleted plasma and per antibody.

Proteomic Analysis of Hsp90 Complex Composition

The immunoprecipitates are dissolved in water and SDS-gel loading buffer and resolved by 2D gel electrophoresis (NuPage, Invitrogen). Visible protein spots are excised from silver stained gels and cleaved with trypsin. The resulting peptides and their precursor proteins are identified by 3-D ion trap liquid chromatography/tandem mass spectrometry (LC/MS/MS) and bioinformatics. Shotgun analyses (LC/MS/MS without prior protein fractionation) are also carried out on the various pull-down complexes, which are expected to identify additional client or associated proteins, especially those with low abundances, high pI values, low molecular masses, or hydrophobicity. The sensitivity of capillary LC/MS/MS is routinely calibrated and can detect protein amounts as low as sub-fmol concentrations. MS/MS spectra is searched against human and mouse protein databases using the computer algorithm Sequest and statistical analysis of the data are performed using the software programs PeptideProphet™ and ProteinProphet™. Resultant proteomic datasets are functionally integrated and visualized by signaling pathway network analysis based on Systems Reconstruction technology using the MetaCore™ software, for example.

Example 8

Comparison of Secreted Hsp90α-Associated Molecules Before and after Treatment with BAs to Hsp90α and Hsp90 "Bulk" Associated Molecules The present example concerns comparison of secreted Hsp90α-associated molecules before and after treatment with BAs to Hsp90α and Hsp90 "bulk" associated molecules in whole cell lysates of human tumors propagated in cell culture or as xenografts.

While the above studies are focused on extracellular Hsp90 partner proteins in absence of drug, the composition of Hsp90-complexes in presence of an Hsp90 inhibitor are examined in the whole cell compartment and the extracellular milieu. This is necessary in order to clarify whether extracellular Hsp90α complexes in presence of BAs reflect the composition of those described above or specialized Hsp90-associated molecules that could derive from within the cell after BAs are bound to Hsp90 isoforms. As described above, one may collect whole cell lysates as well as supernatants of serum-free medium from the same set of in vitro experiments, and plasma as well as tumor tissues from the in vivo xenograft studies.

Hsp90 Complexes in SFM and WCL from Cell Lines Before and after BA Treatment

Based on Western blotting and Hsp90α ELISA test results from studies described above, one may perform proteomic analyses of matching WCL and SFM from vehicle control cells (before) and one time point after 17AAG as well as 17DMAG treatment for all cell lines exposed to the respective drug. One may select the time point of maximal Hsp90α secretion by BA sensitive cells into the supernatant, at which no apoptosis is yet evident. This time point will likely be 24 hrs after drug exposure, for example. The WCL and SFM of three independently performed treatments are pooled and IPs with Hsp90 antibodies performed from 100 µg total cellular protein as described above. 17DMAG samples are included in these studies in order to test whether or not the composition of Hsp90-complexes after drug treatment differs dependent on the BA used.

Hsp90 Complexes in Plasma and Tumor from Mice Before and after 17AAG Treatment

One may select plasma and matching tumor tissue lysates from xenograft experiments described elsewhere herein. One may examine one control (before) and one post-treatment sample per xenograft model. The post-treatment specimens (plasma and tumor) are taken from the time point at which the highest secretion of Hsp90α is observed in BA responsive tumor models by StressXpress ELISA. Plasma and tumor lysates from three mice each are pooled and depleted of high-abundance plasma proteins as described elsewhere herein. IPs with Hsp90 antibodies are performed from 100 µl plasma and 100 µg total protein of tumor lysates Proteomic Analysis of Hsp90 Complex Composition Immuno-complexes are treated and analyzed.

Exemplary Alternative Embodiments

Other studies described herein allows one to conclude whether secretion of Hsp90α serves as a marker of BA response in vitro and in vivo, and the specificity of this action based on an informative (statistically powered) set of experiments. Proteomic analyses of intra and extracellular Hsp90-complexes in absence and presence of BA further confirms the specificity of Hsp90 antibodies and gives an insight into Hsp90α binding proteins/partner molecules that are additional biomarkers of BA activity, in specific embodiments of the invention. As an alternative approach, one will perform Hsp90α ELISA assays with banked plasma samples and compare these results with the data from MDA-MD-231 experiments with 17AAG. This allows one to test whether 17AAG and 17DMAG treatments have similar effects on Hsp90α in vivo and to compare in vitro 17DMAG data described elsewhere herein to in vivo results.

In embodiments wherein shotgun and immunoprecipitation-based methods will miss weak protein:protein interactions, one may detect non-covalent or weak protein-protein interactions between Hsp90α and its clients by employing an alternative approach, for example UV cross-linking followed by BN-PAGE analysis. Briefly, proteins may be cross-linked by the photo-induced cross-linking of unmodified proteins (PICUP) method as developed by Fancy et al. (1999). It has been demonstrated that several closely-associated proteins can be linked covalently by the PICUP method, which entails photolysis in the presence of ruthenium (II) trisbipyridyl dication (Ru(II) bpy32+ and ammonium persulfate (Fancy and Kodadek, 1999; Denison and Kodadek, 2004). The advantage of using PICUP, in contrast to a chemical cross-linking method, is that the cross-linking is initiated by UV light; thus only thermodynamically stable complexes are cross-linked. The chemical cross-linking method is used as an alternative if the identification of fast binding partners is needed. Cross-linking allows non-covalent protein-protein interactions between Hsp90, its co-chaperones and clients, which could be transient or dependent on specific physiological conditions, to be maintained in long-lived covalent complexes that maintain structural information during subsequent purification, enrichment, and analysis. Cross-linked multi-protein complexes are separated by Blue-native poly-acrylamide gel electrophoresis (BN-PAGE) (Swamy et al., 2006). Bands determined not to be representative of non-specific complexes are excised from silverstained gels and subjected to in-gel enzymatic digestion with trypsin followed by liquid chromatography/tandem mass spectrometry (LC-MS/MS) analysis. In contrast to most gel-based proteomic approaches, the sensitivity of capillary LC/MS/MS is routinely calibrated and can detect protein concentrations as low as sub-fmol concentrations. MS/MS spectra are searched against a mouse and human protein database using the computer algorithm Sequest and statistical analysis of the data is performed using the software programs PeptideProphet™ and ProteinProphet™.

Example 9

Assessment of Hsp90α as a Biomarker for Detection, Prediction and Measurement of Response to BAs in Patients The preclinical studies described elsewhere herein provide a clear basis to interpret evidence of Hsp90α expression in patient derived plasma. In some embodiments, one can utilize plasma both from patients not undergoing treatment with BAs and normal individuals. In another embodiment, data from the ongoing phase I clinical trial of sorafenib and 17AAG in patients with solid tumors (FIG. 4) is further characterized by adding banked plasma samples from patient cohorts that have been treated with BAs.

Example 10

Comparison of Hsp90α Plasma Levels in Cancer Patients with Hsp90α Levels from Banked Plasma from Non-Tumor Bearing Hosts The present example concerns comparison of Hsp90α plasma levels in cancer patients with Hsp90α levels from banked plasma from non-tumor bearing hosts, for example.

Source of Plasma Samples

Banked plasma that has expired for human clinical use in transfusion is obtained from a blood bank. Hsp90α plasma levels are defined in 50 such specimens, for example. Fifty plasma specimens are collected from patients undergoing treatment for various malignancies, for example.

Hsp90α StressXpress ELISA

The Hsp90α ELISA assay as described elsewhere herein is performed for each plasma specimen in triplicate. Patient plasma is diluted 1:25 v/v with sample diluent provided with the StressXpress kit. A dilution of 1:25 was found to be optimal for assaying plasma Hsp90α in human samples (FIG. 4). Assays are processed and developed as outlined elsewhere herein.

Sample Size and Statistical Analysis

The proposed sample size (number of specimen, assuming one specimen per patient at one given time point) is derived based on comparing the Hsp90α levels between the cancer and non-cancer groups. Using estimates from xenograft data (FIG. 5) that demonstrate an elevation in Hsp90α of roughly 3 standard deviations, one may conservatively target the sample size and power of the study to detect a difference of 0.75 of a standard deviation between the cancer and non-cancer groups. With a two-sided test on Hsp90α levels (or its normalizing transformation), at least 29 specimen from 29 different patients are needed to detect such a difference at 5% significance level with 80% power. If approximate normality can be achieved with transformation, the Hsp90α levels are compared using a two sample t test for the cancer versus non-cancer groups. If not, nonparametric test is used for analysis. Given that Hsp90α plasma concentrations may depend on tumor size/tumor burden, in specific embodiments of the invention a multiple regression model may be used to assess the difference of Hsp90α levels while adjusting for tumor size.

Example 11

Measurement of Hsp90α Levels in Plasma of Tumor Bearing Hosts Before and after Treatment with BAs The present example concerns measuring Hsp90α levels in plasma of tumor bearing hosts before and after treatment with BAs.

Source of Pre- and Post-Treatment Plasma Samples

Plasma from patients who have already consented on clinical study protocols may be used. This protocol may comprise one part of the study population; this accounts for approximately forty paired samples pre/post 17AAG treatment.

A second source of samples are provided that consists of approximately 100 plasma samples from pre to 24 hours after a BA (17AAG or 17DMAG) administration to human subjects. Approximately eighteen pediatric patient samples are included.

Hsp90α StressXpress ELISA

The Hsp90α ELISA assay as described in detail elsewhere herein is performed for each plasma specimen in triplicate. Patient plasma is diluted 1:25 v/v with sample diluent provided with the StressXpress kit. A dilution of 1:25 was found optimal for assaying plasma Hsp90α in human samples (FIG. 4). Assays are processed and developed as outlined elsewhere herein.

Data Evaluation and Statistical Analysis

Plasma is collected according to standard operating procedures from already registered patients on IRB approved clinical trials. The samples once received are assayed as de-identified specimens. Upon completion of the Hsp90α ELISA assays, observational correlation with clinical course, nature of the underlying tumor (size), sites of metastasis, and response or lack thereof to ansamycin treatment are recorded, and observational and exploratory analyses are undertaken. Demographic information regarding each patient are stored in a secure, dedicated database.

The proposed sample size (number of specimen, assuming one specimen per patient at one given time point) is derived based on comparing the Hsp90α levels between the cancer and non-cancer groups. With a two-sided test on the Hsp90α levels (or its normalizing transformation), 29 specimens from 29 different patients are needed to detect such a difference at 5% significance level with 80% power. Since post treatment samples are matched with pre-treatment specimen, 29 patients will have 80% power to detect even smaller difference (0.55 of the standard deviation) at the 5% significance level. If approximate normality can be achieved with transformation, the Hsp90α levels are compared using a pair t test for paired samples. If not, nonparametric test are used for analysis. Given that Hsp90α plasma concentrations may depend on tumor size/tumor burden, a multiple regression model may be used to assess the difference of Hsp90α levels while adjusting for tumor size.

Comparison of In Vitro, In Vivo and Clinical Data.

When all Hsp90α measurements from in vitro cell line studies, in vivo xenograft experiments and patient plasma samples are collected, one may perform an overall data analysis and create a pharmacodynamics-based mathematical model that could be used to predict "optimal" time of BA exposure; impact of tumor weight and pre-treatment Hsp90α concentrations, or composition of Hsp90α complexes on response to BAs is employed. Pharmcodynamic modeling approaches similar to those developed by Simeoni and colleagues (Denison and Kodadek, 2004) may be utilized.

Exemplary Alternative Embodiments

In order to assess the potential of Hsp90α as a biomarker for detection, prediction and measurement of response to BAs in patients, one may be set to assay a target of 50 plasma specimens to be collected from patients undergoing treatment for various malignancies and banked plasma that has expired for human clinical use from normal subjects. In specific aspects of the invention, long term banking and the anticoagulant used to obtain plasma might impact HspP90α levels. Because one would prospectively collect plasma from cancer patients and also use plasma collected as part of an ongoing sorafenib/17AAG trial that is post-BA treatment, for example, problems with Hsp90α stability upon long term banking and multiple freeze thawing may become evident. In this embodiment, one may evaluate the Hsp90α data from clinical samples not as one, but in multiple sets that differentiate for time of collection and the submitting institution.

The measurement of plasma Hsp90α as a biomarker of response to benzoquinone ansamycin (BA) analogs is novel. The inventors were the first to make this observation in serum-free medium from BA-sensitive cell lines. Moreover, the concept that plasma Hsp90α isoform and/or its associated binding molecules can serve as a marker of the presence and of the overall burden of tumor in an organism and is a useful biomarker for tumor detection and prediction of whether a patient will respond or not to BAs is also innovative. The present invention provides a long-awaited biomarker to aid treatment decision making and response prediction for Hsp90 inhibitory agents.

Example 12

Athymic Nude Mice Bearing Human Tumor Xenografts Release Hsp90α into their Plasma To ascertain the presence of HSP90α in plasma of athymic nude mice bearing human tumor xenografts, the following exemplary samples and methods were employed:

Nude Mouse Xenografts.

Human tumor xenografts were established from cell lines and kept in serial passage until stable growth. Adult athymic Ncr nude mice 6-8 weeks old were supplied by the Animal Production Facility at NCI Frederick. Tumors in passages 3-7 were implanted subcutaneously in both flanks. Blood was obtained post mortem from the axillary vein and collected into tubes containing sodium citrate. Plasma was separated by centrifugation. Tumor volumes were measured with a caliper just prior to terminating the animals. Tumor volumes were calculated using the formula (length×width2)/2, where length is the longest dimension and width the smallest dimension perpendicular to the length.

Human tumor xenografts were established from the following exemplary cell lines: Prostate Cancer (PC-3 and C81); Breast Cancer (Hs578T, MCF-7, and MCF-7-Her2-18); and Melanoma (MEXF276L and MEXF514L).

Hsp90α levels were determined by ELISA assay. ELISA assays were performed using the StressXpress Hsp90α ELISA Kit (Stressgen; Ann Arbor, Mich.). Human and xenograft plasma samples of 10 μL were added to sample diluent buffer and assayed in duplicate in the antibody-coated 96-well plate. After incubation at room temperature for one hour, wells were washed 6 times with washing buffer. 100 uL HRP conjugate was added to wells and incubated for one hour. Wells were washed 6 times, 100 uL TMB substrate was added to each well, and the plate was incubated for 20 minutes. Absorbance was measured at 450 nm on a plate reader. A HSP90α standard curve was plotted and sample concentrations were calculated as ng/mL.

Figure 7:
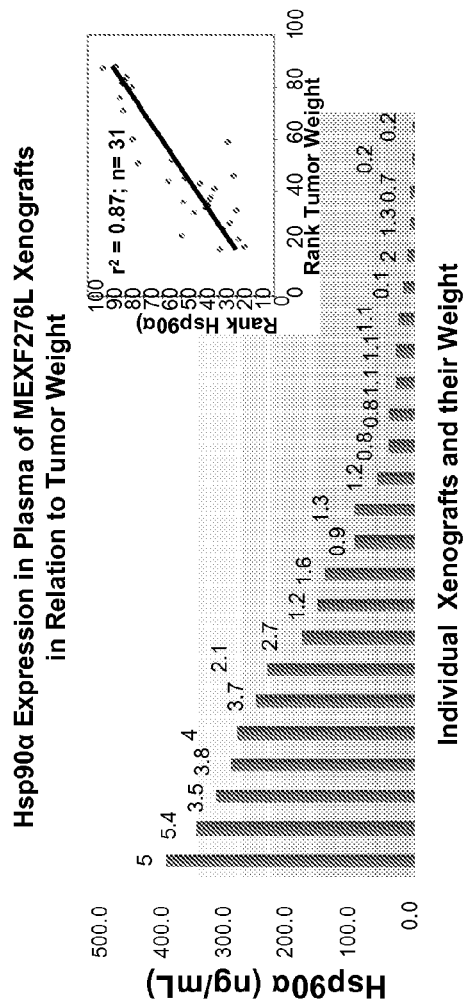
FIG. 7A demonstrates rank correlation and regression analysis comparing tumor weight in grams to Hsp90α plasma levels in ng/mL; r2=0.8 over all tumors (n=91).
FIG. 7B shows the following: Insert: Rank correlation as in A for melanoma xenograft MEXF276L; r2=0.87 (n=31). Bar graph shows Hsp90α levels expressed in ng/mL for individual MEXF276L xenografts and the corresponding tumor weights in grams given on top of each bar.
Figure 7:
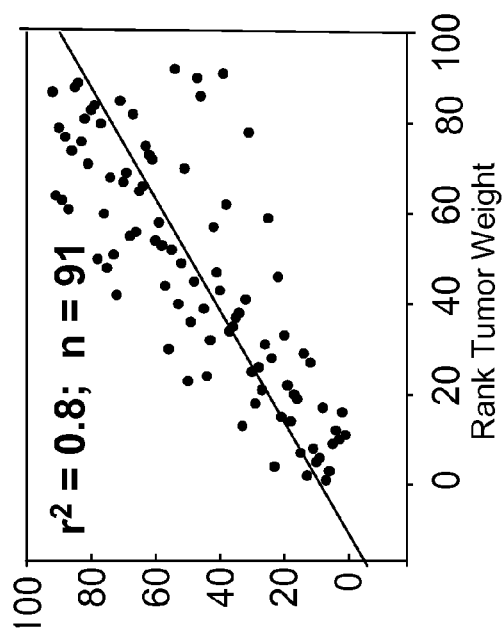

Ninety-one human tumor xenografts including melanoma, prostate and breast cancers were evaluated for tumor weight at time of termination and Hsp90α levels determined. In order to correlate these two parameters, values were ranked and ranks subjected to a Spearman rank correlation test where r values above 0.5 are considered a significant correlation. As shown in FIG. 7A, the correlation coefficient over all three tumor types comparing rank HSP90α to rank tumor weight, was highly significant with a $r^2=0.8$. Within the three tumor types, breast cancer had a $r^2=0.74$ (n=30), the prostate cancer $r^2=0.66$ (n=21), and the $r^2$ for MEXF276L was 0.87 (n=31, FIG. 7B). Clearly the levels of HSP90α in plasma were proportional to the tumor weight (FIG. 7B). A larger tumor size was associated with higher HSP90α plasma levels.

Example 13

Human Hsp90α is Released into the Plasma of Nude Mice Bearing Melanoma Xenografts after Treatment with 17-AAG and into the Plasma of Patients after 17-AAG Treatment Nude mouse xenografts of the melanoma cell lines MEXF276L and MEXF514L were established as in Example 12, and fragments transplanted into 8 nude mice for each line. When tumors reached an approximate size of 250-500 mm³, animals were treated with vehicle control or received 17-AAG at 60 mg/kg/d given as twice daily doses of 30 mg/kg intra-peritoneally. Experiments with MEXF 276LXenografts were performed twice. Blood was collected from the tail vein into tubes containing sodium citrate at base line (day −1), at 24 hours, 48 hrs and 72 hrs after treatment with a single total does of 60 mg/kg/d 17-AAG. The time points were taken after the last 17-AAG injection.

Figure 8:
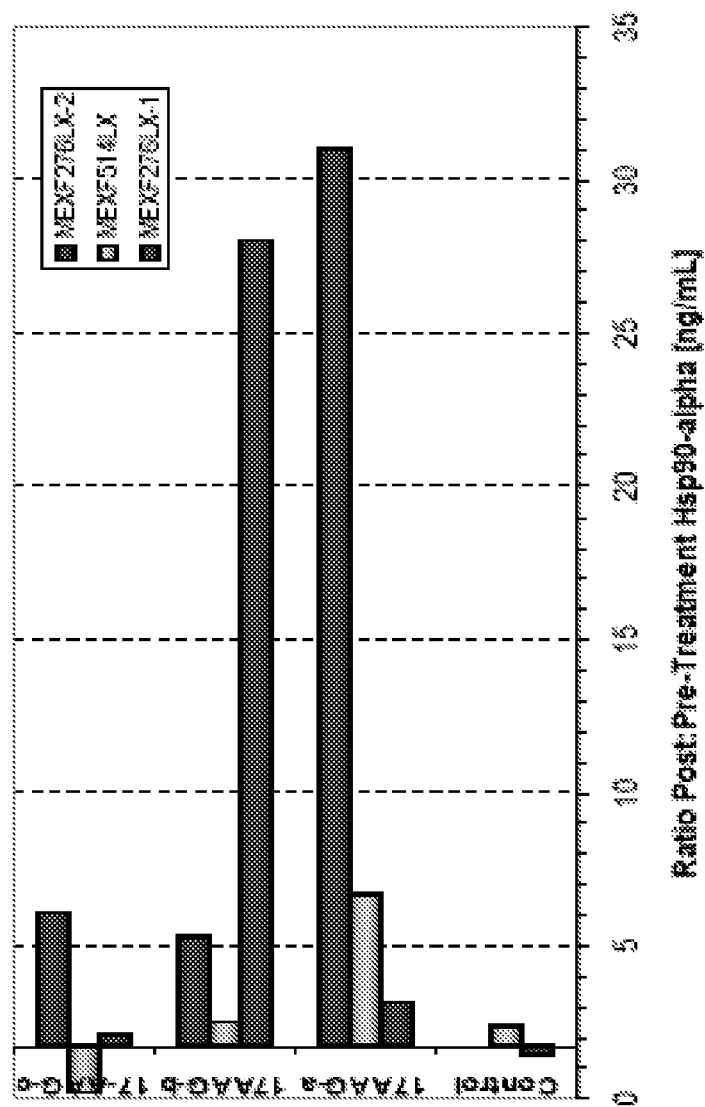
FIG. 8 shows that in nude mice bearing MEXF276L (responding, red) and MEXF514L (non-responding, grey) xenografts, circulating Hsp90α was detected in plasma by ELISA assay (control) and was strongly induced 72 hrs after 17-AAG in MEXF276LX only. Data are displayed as ratio between pre- and post 17-AAG Hsp90α levels. The cut-off for response and resistance was set at a ratio of 1.7. 17AAG-a, -b, -c corresponds to 24, 48 and 72 hrs.

Approximately 100 μl blood was available through tail vein puncture, the 72 hr time point was collected by exsanguinations/cardiac puncture. Blood was processed into plasma and plasma subjected to ELISA analysis as described in Example 12. The data are shown in FIG. 8. The inventors have previously characterized the human melanoma models for Hsp90 and client protein expression, and were able to define MEXF276L as an intrinsically responsive and MEXF514L as a resistant cell line to 17-AAG. It was found that pre 17-AAG Hsp90α was detected in tumor-bearing mice (FIG. 8), but that treatment with 17-AAG resulted in an increase in plasma Hsp90α in most cases (FIG. 8). Interestingly, the 17-AAG sensitive melanoma (red bars) released consistently much higher Hsp90α levels into plasma than the resistant melanoma MEXF514.

In addition to animal experiments, the inventors have collected and processed blood samples for 11 patients that were enrolled into the ongoing NCI clinical trial NCI-6972: A Phase 1 Dose Escalation Study of 17-AAG [NSC 330507] and Bay 43-9006 [NSC 724772, IND #69,896] Administered in Patients with Pre-treated Advanced Solid Tumors.

Figure 9:
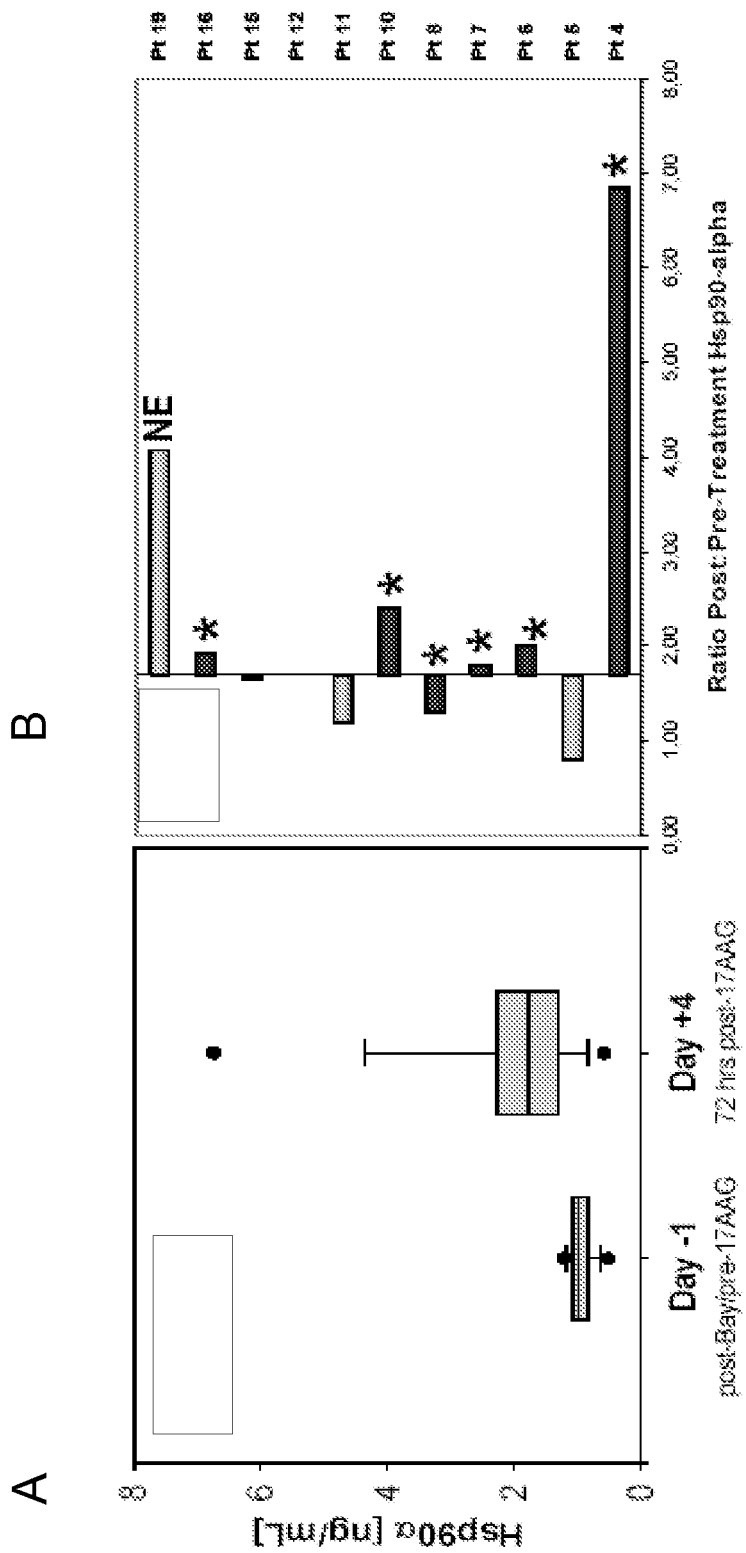
FIG. 9A demonstrates Hsp90α levels in pre- (day −1) and post- (72 hrs, day 4) treatment cancer patients. The induction is significant (p=0.0287).
FIG. 9B shows that data are displayed as ratio between pre- and post 17-AAG Hsp90α levels (compare to FIG. 8). The cut-off for response and resistance was set at a ratio of 1.7. Asterisk indicates that this patient had an objective clinical response to the treatment regimen.

Plasma was analyzed for the circulating isoform of Hsp90, namely Hsp90α (FIGS. 4 and 9). It was found that the induction of Hsp90α (>1.7 pre:post-treatment ratio) was significantly and specifically correlated to response in patients (FIG. 9B, p=0.0287; and C, red bars=responders, aster=stable disease). Importantly, in the clinical study, blood (plasma) is taken at base line (no treatment) and day −1, which is after 14 days of Bay 43-9006. For an individual patient, most day −14 and day −1 plasma Hsp90α levels were identical (FIG. 4) indicating that Bay 43-9006 has no effects on Hsp90α and thus, modulations seen on day +4 are 17-AAG specific.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PUBLICATIONS

Banerji U, O'Donnell A, Scurr M, Pacey S, Stapleton S, Asad Y, Simmons L, Maloney A, Raynaud F, Campbell M, Walton M, Lakhani S, Kaye S, Workman P, Judson I. Phase I pharmacokinetic and pharmacodynamic study of 17-allylamino, 17-demethoxygeldanamycin in patients with advanced malignancies. J Clin Oncol. 2005 Jun. 20; 23(18):4152-61.

Birle D, Wright J, Siu L, Moore M, Oza A. A Phase II Trial with Pharmacodynamic Endpoints of the Burger, A. M. Highlights in experimental therapeutics. Cancer Lett. Apr. 26; [Epub ahead of print], 2006.

Burger, A. M., Fiebig, H. H., Stinson, S. F., Sausville, E. A. 17-(allylamino)-17-demethoxy-geldanamycin activity in human melanoma models. Anticancer Drugs 15: 377-387, 2004

D. Strumberg, Preclinical and clinical development of the oral multikinase inhibitor sorafenib in cancer treatment. Drugs Today 41 (2005) 773-784.

Dalton W W, Friend S H. Cancer biomarkers—an invitation to the table. Science 321: 1165-1168, 2006.

Daniel R. Ciocca and Stuart K. Calderwood. Heat shock proteins in cancer: diagnostic, prognostic, predictive, and treatment implications. Cell Stress & Chaperones (2005) 10 (2), 86-103

DeBoer C, Meulman P A, Wnuk R J, Peterson D H (1970) Geldanamycin, a new antibiotic. J Antibiot (Tokyo) 23:442-447.

Denison C, Kodadek T. Toward a general chemical method for rapidly mapping multi-protein complexes. J Proteome Res 3:417-25, 2004.

Eiseman J L, Lan J, Lagattuta T F, Hamburger D R, Joseph E, Covey J M, Egorin M J. Pharmacokinetics and pharmacodynamics of 17-demethoxy 17-[[(2-dimethylamino)ethyl] amino]geldanamycin (17DMAG, NSC 707545) in C.B-17 SCID mice bearing MDA-MB-231 human breast cancer xenografts. Cancer Chemother Pharmacol. 2005 January; 55(1):21-32.

Eustace B K, Sakurai T, Stewart J K, Yimlamai D, Unger C, Zehetmeier C, Lain B, Torella C, Henning S W, Beste G, Scroggins B T, Neckers L, Ilag L L, Jay D G. Functional proteomic screens reveal an essential extracellular role for hsp90 alpha in cancer cell invasiveness. Nat Cell Biol. 6:507-514, 2004.

Fancy, D. A., and Kodadek, T. Chemistry for the analysis of protein-protein interactions: rapid and efficient cross-linking triggered by long wavelength light. Proc Natl Acad Sci USA 96:6020-4, 1999.

Fiebig, H. H., Burger, A. M.: Human tumor xenografts and explants. In: Teicher, B. A. (Ed.) Animal Models in Cancer Research, pp. 113-137, The Humana Press Inc., Totowa, N.J.-USA, 2001.

Grem J L, Morrison G, Guo X D, Agnew E, Takimoto C H, Thomas R, Szabo E, Grochow L, Grollman F, Hamilton J M, Neckers L, Wilson R H. Phase I and pharmacologic study of 17-(allylamino)-17-demethoxygeldanamycin in adult patients with solid tumors. J Clin Oncol. 2005 Mar. 20; 23(9):1885-93.

Hollingshead, M., Alley, M., Burger, A. M., Borgel, S., Pacula-Cox, C., Fiebig, H. H., Sausville, E. A. In vivo anti-tumor efficacy of 17-DMAG (17-dimethylaminoethylamino-17-demethoxygeldanamycin hydrochloride), a water-soluble geldanamycin derivative. Cancer Chemother. Pharmacol. 56: 115-125, 2005

Hong Zhang, Daun Chung, Yong-Ching Yang, Laura Neely, Steven Tsurumoto, Junhua Fan, Lin Zhang, Kamal A, Boehm M F, Burrows F J. Therapeutic and diagnostic implications of Hsp90 activation. Trends Mol. Med. 2004 June; 10(6):283-90.

Kamal A, Thao L, Sensintaffar J, Zhang L, Boehm M F, Fritz L C, Burrows F J. A high-affinity conformation of Hsp90 confers tumour selectivity on Hsp90 inhibitors. Nature. 2003 Sep. 25; 425(6956):407-10.

Kaur, G., Belotti, D., Burger, A. M., Nielson-Fisher, K., Borsotti, P., Riccardi, E., Tillainathan, J., Hollingshead, M., Sausville, E. A, Giavazzi, R. Anti-angiogenic properties of 17-(dimethyl amino ethyl amino)-17-methoxygeldanamycin (NSC707545, 17-DMAG): an orally bioavailable Hsp90 modulator. Clinical Cancer Res. 10: 4813-4821, 2004.

Lesne S, Koh M T, Kotilinek L, Kayed R, Glabe C G, Yang A J, Gallagher M and Ashe K H. A specific amyloid-β protein assembly in the brain impairs memory. Nature 440:352-7, 2006.

Mackay H, Hedley D, Major P, Townsley C, Mackenzie M, Vincent M, Degendorfer P, Tsao M S, Nicklee T, Marco Biamonte, John Brekken, Karen Lundgren, and Francis Burrows Identification of new biomarkers for clinical trials of Hsp90 inhibitors. Mol Cancer Ther 2006; 5(5): 1256-64]

Matthew P. Goetz, David Toft, Joel Reid, Matthew Ames, Bridget Stensgard, Stephanie Safgren, Araba A. Adjei, Jeff Sloan, Pamela Atherton, Vlad Vasile, Sandra Salazaar, Alex Adjei, Gary Croghan, Charles Erlichman Phase I Trial of 17-Allylamino-17-Demethoxygeldanamycin in Patients With Advanced Cancer. Journal of Clinical Oncology, Vol 23, No 6 (Feb. 20), 2005: pp. 1078-1087.

Munster P N, Srethapakdi M, Moasser M M, Rosen N. Inhibition of heat shock protein 90 function by ansamycins causes the morphological and functional differentiation of breast cancer cells. Cancer Res. 2001 Apr. 1; 61(7):2945-52.

Nimmanapalli R, O'Bryan E, Bhalla K. Geldanamycin and its analogue 17-allylamino-17-demethoxygeldanamycin lowers Bcr-Abl levels and induces apoptosis and differentiation of Bcr-Abl-positive human leukemic blasts. Cancer Res. 2001 Mar. 1; 61(5):1799-804.

Picard, D. Hsp90 invades the outside. Nature Cell Biol. 6, 479-480 (2004).

Pratt W B, Toft D O. Regulation of signaling protein function and trafficking by the hsp90/hsp70-based chaperone machinery. Exp Biol Med (Maywood). 2003 February; 228(2):111-33.

Price J T, Quinn J M, Sims N A, Vieusseux J, Waldeck K, Docherty S E, Myers D, Nakamura A, Waltham C, Gillespie M T, Thompson E W. The heat shock protein 90 inhibitor, 17-allylamino-17-demethoxygeldanamycin, enhances osteoclast formation and potentiates bone metastasis of a human breast cancer cell line. Cancer Res 65:4929-38, 2005.

Proteasome Inhibitor Bortezomib in Patients with Metastatic Colorectal Cancer Clin Cancer Res 11: 5526-5533, 2005.

R. K. Ramanathan, D. L. Trump, J. L. Eiseman, C. P. Belani, S. S. Agarwala, E. G. Zuhowski, J. Lan, D. M. Potter, S. P. Ivy, S. Ramalingam, A. M. Brufsky, M. K. K. Wong, S. Tutchko, and M. J. Egorin Phase I Pharmacokinetic-Pharmacodynamic Study of 17-(Allylamino)-17-Demethoxygeldanamycin (17AAG, NSC 330507), a Novel Inhibitor of Heat Shock Protein 90, in Patients with Refractory Advanced Cancers. Clin. Cancer Res., May 1, 2005; 11(9): 3385-3391.

Sakagami M, Morrison P, Welch W J. Benzoquinoid ansamycins (herbimycin A and geldanamycin) interfere with the maturation of growth factor receptor tyrosine kinases. Cell Stress Chaperones. 1999 March; 4(1):19-28.

Simeoni M, Magni P, Cammia C, De Nicolao G, Corci V, Pesenti E, Germani M, Poggesi I, Rocchetti M. Predictive pharmacokinetic-phamacodynamic modelling of tumor growth kinetics in xenograft models after administration of anticancer agents. Cancer Res 64: 1094-1101, 2004.

Smith, V., Sausville, E. A., Camalier, R. F., Fiebig, H. H., Burger, A. M. Comparison of 17-dimethylaminoethylamino-17-demethoxy-geldanamycin (17DMAG) to 17-allylaminodemethoxygeldanamycin (17AAG) in vitro: effects on Hsp90 and client proteins in melanoma models. Cancer Chemother. Pharmacol. 56: 126-137, 2005

Solit D B, Zheng F F, Drobnjak M, Munster P N, Higgins B, Verbel D, Heller G, Tong W, Cordon-Cardo C, Agus D B, Scher H I, Rosen N. 17-Allylamino-17-demethoxygeldanamycin induces the degradation of androgen receptor and HER-2/neu and inhibits the growth of prostate cancer xenografts. Clin Cancer Res. 2002 May; 8(5):986-93.

Sreedhar A S, Kalmar E, Csermely P, Shen Y F. Hsp90 isoforms: function, expression and clinical importance. FEBS Letters 562: 11-15, 2004.

Stebbins C, Russo A, Schneider C, Rosen N, Hartl F, Pavletich N (1997) Crystal structure of an Hsp90-geldanamycin complex: targeting of a protein chaperone by an antitumor agent. Cell 89:239.

Swamy M, Siegers G M, Minguet S, Wollscheid B, Schamel W A. Blue Native Polyacrylamide Gel Electrophoresis (BN-PAGE) for the identification and analysis of multiprotein complexes Sci. STKE, 345: p 14, 2006.

Thomas S N., Lu B, Nikolskaya, T., Yuri N., and Yang A J. MudPIT (Multidimensional Protein Identification Technology) for identification of post-translational protein modifications in complex biological mixtures. In Redox proteomics: from protein modifications to cellular dysfunction and diseases. Wiley Inter Science, 2006.

Veerasamy, S., Malone, K., Sausville, E. A., Burger, A. M. Response of melanoma cells to 17-allylaminogeldanamycin is associated with modulation of extracellular Hsp90 and MMP2 Proc Amer Assoc Cancer Res 47: 1154, 2006.

Whitesell L, Mimnaugh E G, De Costa B, Myers C E, Neckers L M. Inhibition of heat shock protein HSP90-pp 60v-src heteroprotein complex formation by benzoquinone ansamycins: essential role for stress proteins in oncogenic transformation. Proc Natl Acad Sci USA. 1994 Aug. 30; 91(18):8324-8.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of monitoring whether or not a cancer is responsive to a melanoma cancer therapy in an individual in need of therapy for melanoma and that has been diagnosed with melanoma, comprising:
   (1) determining the level of Hsp90 in the plasma or serum of the individual in need of therapy for melanoma prior to administration of the melanoma cancer therapy;
   (2) administering to the individual a desired dosage of the melanoma cancer therapy;
   (3) determining the level of Hsp90 in the plasma or serum of the individual following administration of the melanoma cancer therapy;
   (4) determining whether there is an increase in the level of Hsp90 in step (3) compared to step (1); and
   (5) classifying an individual as being responsive to the melanoma cancer therapy when there is an increase in the level of Hsp90, wherein the melanoma cancer therapy is a Hsp90-interacting therapy comprising an inhibitor of Hsp90 comprising one or more benzoquinoid ansamycins.

2. The method of claim 1, further defined as obtaining a sample comprising blood from the individual and processing the sample to obtain plasma or serum.

3. The method of claim 1, wherein the Hsp90 is Hsp90α.

4. The method of claim 1, wherein the Hsp90 is extracellular.

5. The method of claim 1, wherein the Hsp90-interacting melanoma cancer therapy comprises 17-allylamino, 17 demethoxy geldanamycin, CF237, EC69, EC97, or PU3.

6. The method of claim 1, wherein the increase in the level of Hsp90 is at least two-fold.

7. The method of claim 1, wherein the level of Hsp90 in the plasma or serum is determined by measuring Hsp90 protein levels.

8. The method of claim 1, further comprising the step of determining the level of an Hsp90-associated molecule.

* * * * *

UNITED STATES PATENT AND TRADEMARK OFFICE
CERTIFICATE OF CORRECTION

PATENT NO. : 8,580,519 B2  Page 1 of 1
APPLICATION NO. : 12/515770
DATED : November 12, 2013
INVENTOR(S) : Burger et al.

It is certified that error appears in the above-identified patent and that said Letters Patent is hereby corrected as shown below:

In the Specification

Column 1, second paragraph, lines 10-14, please delete the below paragraph and replace with the following:

~~"This invention Was made With government support under NCA-SAIC subcontract number WSU06043; NCI Grant number CA062487; and NCI Grant No. CA129666. The United States Government has certain rights in the invention."~~

This invention was made with government support under grant numbers CA062487 and CA129666 and subcontract number WSU06043 awarded by the National Institutes of Health. The United States Government has certain rights in the invention.

Signed and Sealed this
Fifteenth Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,580,519 B2 | Page 1 of 1 |
| APPLICATION NO. | : 12/515770 | |
| DATED | : November 12, 2013 | |
| INVENTOR(S) | : Burger et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this
Twenty-eighth Day of April, 2015

Michelle K. Lee
*Director of the United States Patent and Trademark Office*